US010603176B2

(12) United States Patent
Arnold et al.

(10) Patent No.: US 10,603,176 B2
(45) Date of Patent: Mar. 31, 2020

(54) IMPLANT AND METHOD FOR POSTERIOR SACROILIAC FUSION

(71) Applicant: SAIL FUSION, LLC, Solana Beach, CA (US)

(72) Inventors: Benjamin Arnold, San Diego, CA (US); Brian Bowman, Carlsbad, CA (US); Kristen Pena, Encinitas, CA (US); Vikas Patel, Denver, CO (US)

(73) Assignee: SAIL FUSION, LLC, Solana Beach, CA (US)

( * ) Notice: Subject to any disclaimer, the term of this patent is extended or adjusted under 35 U.S.C. 154(b) by 110 days.

(21) Appl. No.: 15/653,284

(22) Filed: Jul. 18, 2017

(65) Prior Publication Data
US 2018/0014939 A1   Jan. 18, 2018

Related U.S. Application Data

(60) Provisional application No. 62/363,752, filed on Jul. 18, 2016, provisional application No. 62/448,848, filed on Jan. 20, 2017.

(51) Int. Cl.
| A61B 17/86 | (2006.01) |
| A61F 2/30 | (2006.01) |
| A61B 17/80 | (2006.01) |
| A61B 17/70 | (2006.01) |

(Continued)

(52) U.S. Cl.
CPC ...... *A61F 2/30988* (2013.01); *A61B 17/7059* (2013.01); *A61B 17/809* (2013.01); *A61B 17/8057* (2013.01); *A61B 17/8066* (2013.01); *A61B 17/86* (2013.01); *A61F 2/446* (2013.01); *A61F 2/4455* (2013.01); *A61B 17/863* (2013.01); *A61F 2002/2817* (2013.01); *A61F 2002/3085* (2013.01); *A61F 2002/30168* (2013.01); *A61F 2002/30181* (2013.01); *A61F 2002/30578* (2013.01); *A61F 2002/30622* (2013.01); *A61F 2002/30995* (2013.01)

(58) Field of Classification Search
CPC .............. A61F 2002/30995; A61B 17/7055
See application file for complete search history.

(56) References Cited

U.S. PATENT DOCUMENTS 3,488,779 A * 1/1970 Christensen .......... A61F 2/3099
623/16.11
4,883,488 A * 11/1989 Bloebaum ............... A61F 2/389
623/20.34

(Continued)

FOREIGN PATENT DOCUMENTS

WO   WO-2018017556 A1   1/2018

OTHER PUBLICATIONS

International Search Report and Written Opinion dated Sep. 27, 2017 for International PCT Application No. PCT/US17/42560.
Office action dated Oct. 3, 2019 for U.S. Appl. No. 15/847,727.

*Primary Examiner* — David W Bates
(74) *Attorney, Agent, or Firm* — Wilson Sonsini Goodrich & Rosati

(57) ABSTRACT

An implant and method for posterior sacroiliac fusion having a plate for placement across the posterior surface of the sacroiliac joint, a transverse pin to slide through the plate and transverse the joint as well as provide an aperture to receive bone graft, and a sacral screw to be inserted through the plate.

12 Claims, 26 Drawing Sheets

(51) Int. Cl.
*A61F 2/44* (2006.01)
*A61F 2/28* (2006.01)

(56) References Cited

U.S. PATENT DOCUMENTS

| | | | | |
|---|---|---|---|---|
| 5,300,073 | A * | 4/1994 | Ray | A61B 17/7055 606/250 |
| 9,017,407 | B2 * | 4/2015 | Donner | A61F 2/30988 623/17.11 |
| 9,066,766 | B2 * | 6/2015 | Raven, III | A61B 17/8061 |
| 9,381,045 | B2 * | 7/2016 | Donner | A61B 17/1626 |
| 9,668,783 | B2 * | 6/2017 | Goel | A61B 17/7064 |
| 9,700,356 | B2 * | 7/2017 | Donner | A61B 17/68 |
| 9,826,986 | B2 * | 11/2017 | Donner | A61B 17/1659 |
| 2008/0021454 | A1 * | 1/2008 | Chao | A61B 17/7044 606/250 |
| 2010/0268228 | A1 * | 10/2010 | Petersen | A61F 2/30988 606/60 |
| 2011/0184519 | A1 * | 7/2011 | Trieu | A61B 17/7055 623/17.11 |
| 2011/0230966 | A1 * | 9/2011 | Trieu | A61B 17/562 623/17.12 |
| 2011/0238181 | A1 * | 9/2011 | Trieu | A61B 17/1735 623/17.11 |
| 2011/0264229 | A1 * | 10/2011 | Donner | A61F 2/30988 623/18.11 |
| 2012/0022595 | A1 * | 1/2012 | Pham | A61B 17/7032 606/278 |
| 2012/0191191 | A1 * | 7/2012 | Trieu | A61B 17/683 623/17.11 |
| 2012/0323285 | A1 | 12/2012 | Assell et al. | |
| 2014/0135850 | A1 * | 5/2014 | Parent | A61B 17/68 606/304 |
| 2014/0200618 | A1 * | 7/2014 | Donner | A61B 17/1757 606/281 |
| 2014/0277460 | A1 * | 9/2014 | Schifano | A61F 2/4611 623/17.11 |
| 2015/0173805 | A1 * | 6/2015 | Donner | A61B 17/68 606/279 |
| 2015/0289913 | A1 * | 10/2015 | Vaidya | A61B 17/8066 623/22.12 |
| 2015/0335372 | A1 | 11/2015 | Schifano et al. | |
| 2016/0106477 | A1 * | 4/2016 | Hynes | A61B 17/7044 606/279 |
| 2017/0303938 | A1 * | 10/2017 | Rindal | A61B 17/846 |
| 2018/0177535 | A1 * | 6/2018 | Boulot | A61B 17/7055 |

\* cited by examiner

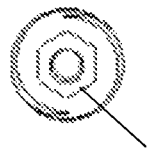
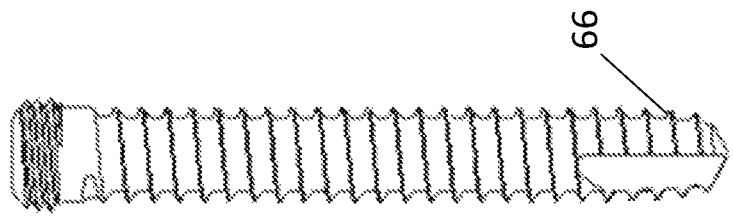
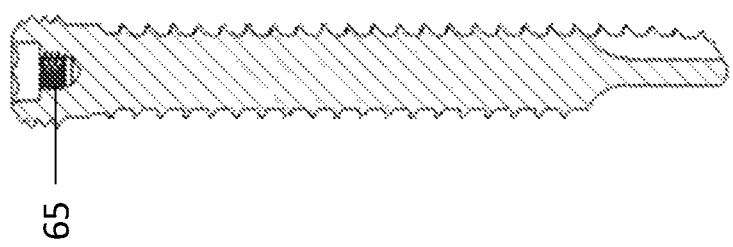
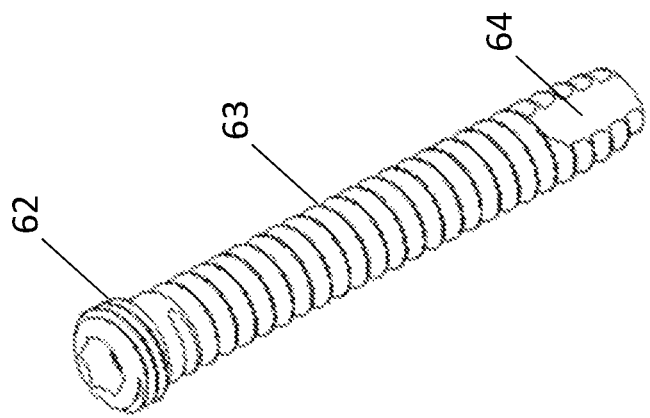
Figure 17D
Figure 17C
Figure 17B
Figure 17A

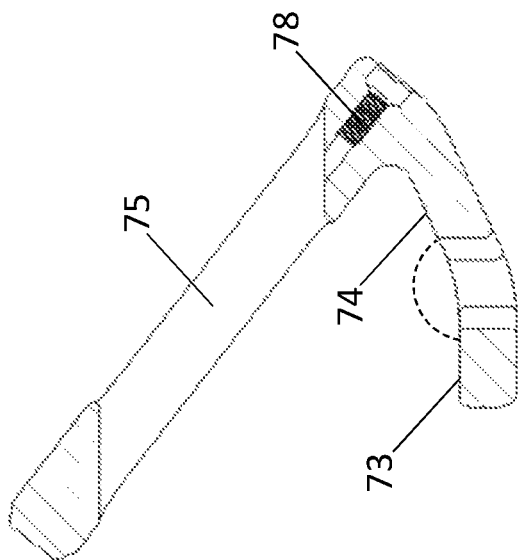
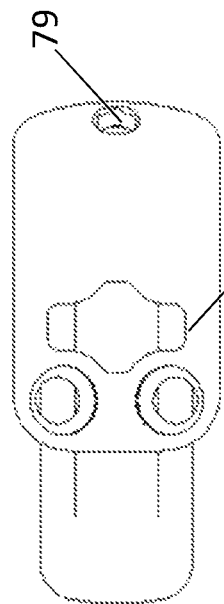
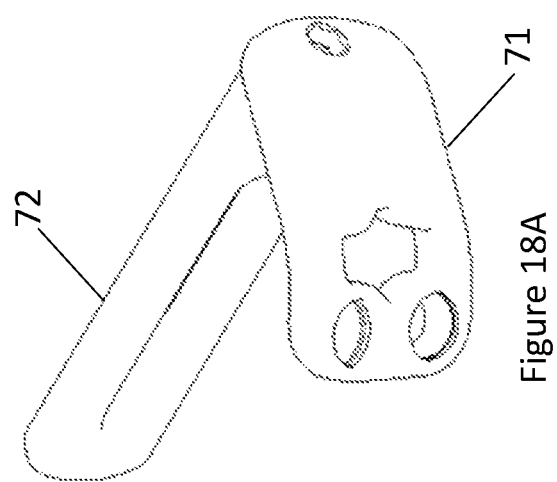
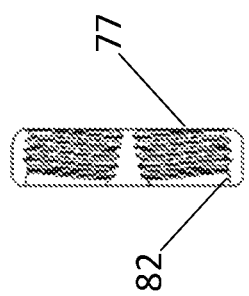
Figure 18A
Figure 18B
Figure 18C
Figure 18D

IMPLANT AND METHOD FOR POSTERIOR SACROILIAC FUSION

CROSS-REFERENCE TO RELATED APPLICATIONS

This application claims priority to U.S. Provisional Patent Application No. 62/363,752 filed on Jul. 18, 2016, as well as U.S. Provisional Patent Application No. 62/448,848 filed on Jan. 20, 2017, each of which is entirely incorporated herein by reference.

BACKGROUND OF THE INVENTION

The sacroiliac (SI) joint is the juncture between the sacrum at the base of the spine and the ilium of the pelvis. The SI joint is a synovial joint in which the sacral surface has hyaline cartilage that moves against fibrocartilage of the iliac surface. The SI joint has irregular elevations and depressions that produce interlocking of the two bones.

Disorders of the SI joint can cause low back and radiating buttock and leg pain. Pain associated with the SI joint can be caused by traumatic fracture dislocation of the pelvis, degenerative arthritis, sacroiliitis, or other degenerative conditions. Contributing factors include post-traumatic injury, accelerated wear/instability after lumbar fusion, post pregnancy pain/instability, and longer life span combined with a more active lifestyle in many patients.

The SI joint is increasingly being recognized as a pain generator as SI joint degenerative disease and instability are being diagnosed and treated more commonly. It is estimated that disorders of the sacroiliac joint are a source of pain for millions of people suffering from back and radicular symptoms.

Surgical treatment of these disorders includes stabilization and/or arthrodesis. Fusion of the SI joint can be accomplished by several different conventional methods encompassing an anterior approach, a posterior approach, and a lateral approach. These procedures typically involve fixation of the sacroiliac joint by placement of one or more trans-sacroiliac implants or by placement of implants into the S1 pedicle and iliac bone.

While these methods have been utilized for fixation and fusion of the SI joint over the past several decades, in certain circumstances challenges with respect to the fixation and fusion of the SI joint may remain unresolved. Many of the SI joint fusion procedures on the market today fixate the SI joint from a challenging lateral approach. Minimally invasive procedures such as these are can be technically difficult requiring extensive surgical training and experience and may result in a substantial incidence of damage to the lumbosacral neurovascular elements. Furthermore, the lateral approach to the SI joint often fixates the joint with multiple implants that go across the joint, not offering a true fusion approach into the SI joint.

Additionally, current techniques and instruments typically allow for either fixation or fusion and thereby do not resolve both issues. Procedures are often performed without adequate removal of the articular joint surfaces or preparation of cortical bone and thereby do not always address the degenerative condition of the SI joint.

Failure to sufficiently stabilize and fuse the SI joint with the implant structures and methods may result in a failure to relieve the condition of the SI joint being treated, leading to continued or recurrent SI joint pain and instability requiring additional surgery.

It would therefore be desirable to provide improved methods, systems, and devices that address at least some of these issues.

SUMMARY OF THE INVENTION

The present disclosure generally relates to medical devices and methods, and more particularly relates to implants and methods for fixation and fusion of the sacroiliac joint.

It would be desirable to address the sacroiliac joint through a posterior approach while delivering both fusion and fixation of the joint. A posterior approach allows for direct visualization of the sacroiliac joint. In examples, the direct visualization of the sacroiliac joint when using a posterior approach is beneficial for effective decortication to create a proper fusion bed. In some embodiments, once the sacroiliac joint has been decorticated, the sacroiliac joint can be fixated with an implant. In some embodiments, the sacroiliac may be fixated with an implant prior to decortication. Optionally, in any embodiments the sacroiliac joint can be pre-packed with bone growth inducing material. Optionally, in any embodiments the sacroiliac joint can be post-packed with bone growth inducing material. Optionally, in any embodiments the traverse pin within the implant may allow for placement of bone growth inducing material extending from the ilium, through the sacroiliac joint, and into the sacrum.

An aspect of the invention provides a sacroiliac joint implant system for fixating and promoting fusion between an ilium, a sacrum, and a sacroiliac joint space. The system comprises a plate/pin component having a plate component and a pin component. The plate component has an iliac portion and a sacral portion, wherein the iliac portion has a first aperture, wherein the sacral portion has a second aperture, and wherein the iliac portion and said sacral portion have an angle between 95-175 degrees disposed therebetween. The pin component is connected with said iliac portion of said plate component, said pin configured for placement through said first aperture, through said ilium, across said sacroiliac joint space, and into said sacrum. The system further comprises a sacral screw inserted into said sacral portion of said plate component, said sacral screw configured for placement through said second aperture, through said sacrum.

Another aspect of the invention provides a sacroiliac joint implant system for fixating and promoting fusion between an ilium, a sacrum, and a sacroiliac joint space. The system comprises a plate having an iliac portion and a sacral portion, wherein said iliac portion has a first aperture, wherein said sacral portion has a second aperture, and wherein said iliac portion and said sacral portion have an angle between 95-175 degrees disposed therebetween. The system also comprises a transverse pin inserted into said iliac portion of said plate, said transverse pin configured for placement through said first aperture, through said ilium, across said sacroiliac joint space, and into said sacrum, said transverse pin comprising a receiving component. Additionally, the system comprises a sacral screw inserted into said sacral portion of said plate, said sacral screw configured for placement through said second aperture, through said sacrum, and secured into said receiving component of said transverse pin.

A further aspect of the invention provides a method of fixation and fusion of a sacroiliac joint comprising an ilium, a sacrum, and a sacroiliac joint space. The method comprises decortating of said sacroiliac joint. The method also comprises broaching a first channel through said ilium, across said sacroiliac joint space, and into said sacrum, wherein said first channel is configured to receive a transverse pin of a sacroiliac joint implant. Additionally, the method comprises providing bone growth inducing material within said sacroiliac joint space. The method also comprises drilling a second channel into said sacrum, wherein said second channel is configured to receive a sacrum screw of said sacroiliac joint implant. The method further comprises placing a plate of said sacroiliac joint implant across said sacroiliac joint space, said place comprising a sacrum portion and an ilium portion. Additionally, the method comprises inserting said transverse pin through said plate and through said first channel. The method further comprises inserting said sacrum screw through said plate and through said second channel.

An additional aspect of the invention provides a method of fixation and fusion of a sacroiliac joint comprising an ilium, a sacrum, and a sacroiliac joint space. The method comprises decorticating the joint space with a rasp. The method also comprises sliding the plate over said rasp. Additionally, the method comprises inserting bone screws on the sacral side of the plate. The method also comprises removing the rasp through the plate. The method further comprises using a box cutter to create a track for the transverse pin. Additionally, the method comprises inserting the transverse pin. Further, the method comprises inserting bone screws on the iliac side.

Some embodiments of the apparatus can provide a plate component for placement over the posterior inferior end of SI joint. In embodiments, the plate component may be integrally connected with a pin component which transversely extends across the SI joint. Embodiments may additionally provide one or more bone screws which slides through the plate components. Optionally, in any embodiments at least one bone screw may be inserted into an opening on the sacral side of the plate, into the sacrum. Optionally, in any embodiments at least one bone screw may be inserted into an opening on the iliac side of the plate, into the sacrum. In some embodiments, the one or more bone screws may be straddle the pin. In some embodiments, one or more bone screws may be threaded into the pin component.

Some embodiments of the apparatus can provide a plate for placement over the posterior inferior end of SI joint. Embodiments may also provide a pin which slides through an opening on the iliac side of the plate and transversely extends across the SI joint. Embodiments may additionally provide a screw which slides through an opening on the sacral side of the plate, into the sacrum. In some embodiments, the screw may thread into the transverse pin.

The present disclosure also relates to a method including marking the joint location with fluoroscopy, creating an incision over the iliac wing, dissecting down to the sacroiliac joint, decorticating the joint space, placing the plate over the posterior inferior end of the sacroiliac joint, drilling a hole through the hole on the iliac side of the plate, into the ilium, through the sacroiliac joint, and into a sacrum, broaching the hole to fit the shape of the transverse pin, inserting the transverse pin into the plate and through the hole, drilling a hole through the hole in the sacral side of the plate and into the sacrum, and inserting the sacral screw into the plate and through the hole and threading the sacral screw into the transverse pin.

Optionally, in any embodiment the implant can provide a plurality of bone ingrowth aperture elements for receiving bone growth material and facilitating fusion of the sacroiliac joint.

Optionally, in any embodiment the methods can include packing the implant with bone growth inducing material before and/or after implantation.

Optionally, in any embodiment the implant can provide an additional device or method to guide the placement of holes in the sacrum and ilium. In embodiments, the plate may preferably be placed after the drilling/broaching of the holes/void. Additionally, the transverse pin may be inserted. Further, the sacral screw may be inserted and threaded into the transverse pin.

Additional optional embodiments will be apparent from the detailed descriptions and the claims herein.

BRIEF DESCRIPTION OF THE DRAWINGS

FIG. 17A is a perspective view of an exemplary embodiment of a bone screw.

FIG. 17B is a cross-section view of the embodiment in FIG. 17A.

FIG. 17C is a front view of the embodiment in FIG. 17A.

FIG. 17D is a top view of the embodiment in FIG. 17B.

FIG. 18A is a perspective view of an exemplary embodiment of the plate/pin.

FIG. 18B is a cross-sectional front view of the embodiment in FIG. 18A.

FIG. 18C is a cross-sectional side view of the embodiment in FIG. 18A.

FIG. 18D is a top view of the plate/pin shown in FIG. 18A.

DETAILED DESCRIPTION OF THE INVENTION

Specific embodiments of the disclosed device and method of use will now be described with reference to the drawings. Nothing in this detailed description is intended to imply that any particular component, feature, or step is essential to the invention.

Figure 1:
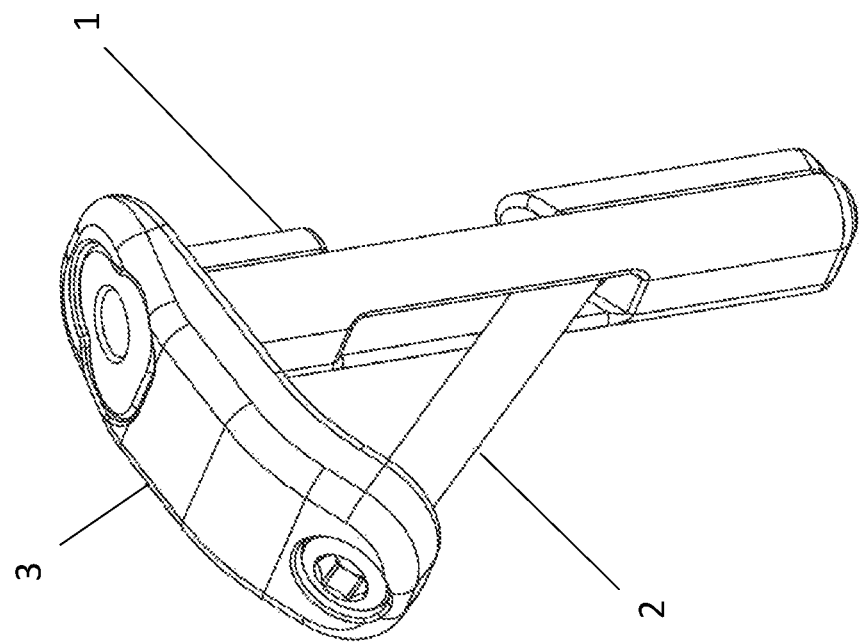
FIG. 1 is a perspective view of an exemplary embodiment of an implant for sacroiliac joint fusion.

FIG. 1 is a perspective view of an exemplary embodiment of an implant for sacroiliac joint fusion. FIG. 1 illustrates an embodiment with optional features, any of which may be optionally used or substituted with other features in other embodiments discussed herein. The embodiment of the implant as provided in FIG. 1 illustrates a transverse pin 1 and a sacral screw 2 that pass through a plate 3. Optionally, in any embodiments components of the implant may be made of stainless steel. Optionally, in any embodiments components of the implant may be made of titanium. Optionally, in any embodiments some components of the implant may be made of stainless steel and some components of the implant may be made of titanium. Optionally, in any embodiments the transverse pin may be made of porous material. Optionally, in any embodiments the transverse pin may be made of porous titanium. Optionally, in any embodiments the transverse pin may be made of porous titanium coated for bone ingrowth.

The implant provided in FIG. 1 may be used to immobilize the sacroiliac joint. In examples, a plate may be rectangular. In additional embodiments, a plate may be circular, triangular, elliptical, or another shape. In some embodiments, a plate may be curved to match the curvature of the sacrum and ilium across the sacroiliac joint. As anatomy may differ between patients, the curvature of a particular plate may differ from patient to patient. Optionally, in any embodiments curvature may be between 95 degrees and 175 degrees Optionally, in any embodiments curvature may be between 120 degrees and 160 degrees. Optionally, in any embodiments a plate of the implant, such as plate 3 as seen in FIG. 1, may contain a cylindrical recess extending through the plate with a countersink on one end of the plate for receiving a sacral screw, such as sacral screw 2, and a recess extending through the plate with a countersink on the opposite end of the plate shaped to receive a transverse pin, such as transverse pin 1. The plate of an implant may be placed across the sacroiliac joint. In particular, the plate of an implant may be placed across the sacroiliac joint such that a portion of the plate is placed against the sacrum, a portion of the plate is placed against the ilium, and a portion of the plate is placed across the sacroiliac joint gap. Additionally, the transverse pin may be placed through its corresponding hole in the plate. Optionally, in any embodiments the transverse pin may be placed with a sliding fit through its corresponding hole in the plate. Optionally, in any embodiments the tranverse pin may be threaded through its corresponding hole in the plate. Further, the sacral screw may be placed through its corresponding hole in the plate. Optionally, in any embodiments the sacral screw may be placed with a sliding fit through its corresponding hole in the plate. Optionally, in any embodiments the sacral screw may be threaded through its corresponding hole in the plate. In examples, the sacral screw may be placed with a fit through it corresponding hold in the plate, through the sacrum, through the aperture in the transverse pin, and then threaded into the shaft of the transverse pin.

Optionally, in any embodiments the sacral screw comprises a cylindrical body and cylindrical head Optionally, in any embodiments, the body may be a different shape, such as a generally square-ish shape or a generally triangular shape, or another example of a different shape. Optionally, in any embodiments the head may be a different shape, such as a generally square-ish shape or a generally triangular shape, or another example of a different shape. Optionally, in any embodiments the head may have a larger diameter than the body. Optionally, in any embodiments the sacral screw may comprise a socket to receive a driver that can rotate the screw. Optionally, in any embodiments the socket is a hex socket. In some embodiments, the socket may be a different shape. In examples, the cylindrical body may consist of a non-threaded portion and threaded distal tip. Optionally, in any embodiments transverse pin 1 may comprise a predominantly triangular body of three intersecting circular regions with one flat side and head 4. Optionally, in any embodiments the transverse pin may comprise a different shape, such as a cylindrical shape or a rectangular box-like shape, among other examples. Optionally, in any embodiments head 4 may be of similar but larger shape than the corresponding body of the traverse pin. The aperture through the main body of transverse pin 1 may consist of a flat upper part and angled lower surface such that it has a smaller opening on one side and a larger opening on the opposite side. Optionally, in any embodiments the angled lower surface by be between 30 degrees and 60 degrees. Optionally, in any embodiments the angled lower surface may be approximately 45 degrees. Optionally, in any embodiments the angled lower surface may be based on an angle of entry that a sacral screw enters when inserted through a plate that has a sacral component that is angled based on geometry of a patient's anatomy. Because of this, the angled lower surface may have an angle that is customized based upon a patient's anatomy. In examples, the angled lower surface may have a receiving component to receive a distal portion of a sacral screw. In some embodiments, transverse pin may comprise a threaded blind hole to receive the distal threaded tip of sacral screw 2. In examples, an implant as described herein can be effectively placed using a posterior surgical approach. In embodiments, the implants may be sized according to the local anatomy. In particular, the implants may be sized accordingly to the local anatomy of particular patients.

Figure 2:
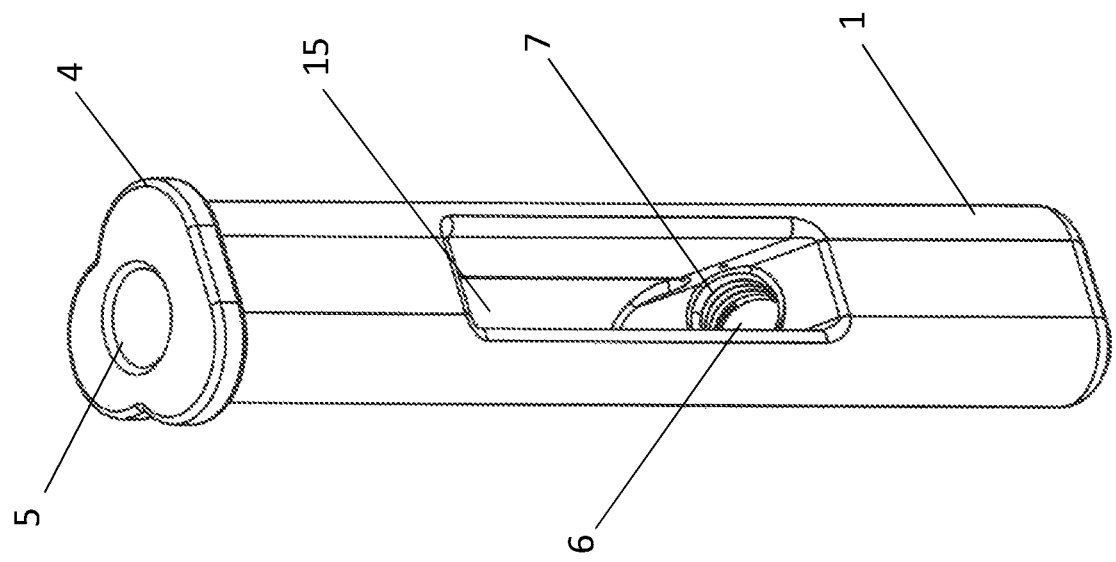
FIG. 2 is a perspective view of an exemplary embodiment of the transverse pin.

FIG. 2 is a perspective view of an exemplary embodiment of the transverse pin, such as transverse pin 1, that may be used in an implant described herein. FIG. 2 illustrates an embodiment with optional features, any of which may be optionally used or substituted with other features in other embodiments discussed herein. FIG. 2 shows a preferred embodiment of transverse pin 1. Transverse pin 1 may comprise a predominantly triangular body of three intersecting circular regions with one flat side and head 4 of similar but larger shape as the corresponding body of traverse pin 1. The head of the traverse pin may engage with a plate of an implant. In examples, a head 4 of traverse pin 1 may engage with plate 3, as shown in FIG. 1. As seen in FIG. 2, a cylindrical hole 5 extends from head 4 to aperture 15. Cylindrical hole 5 may extend from head 4 to aperture 15 so as to allow for packing of the aperture with bone growth inducing material after the transverse pin is implanted and aperture 15 through transverse pin 1 with a flat upper part and angled lower surface such that it has a smaller opening on one side and a larger opening on the opposite side.

Aperture 15 may allow for the insertion of bone growth inducing material. Examples of bone inducing material may include biologics, agents, medical adhesives, bonding cements, and/or bone healing substances. Optionally, in any embodiments the transverse pin may include some features to help contain bone growth inducing material. Optionally, in any embodiments aperture 15 may include retaining walls to help pre-packed bone growth inducing material during transverse pin insertion. Additionally, transverse pin 1 may comprise a threaded, blind hole 6 shaped to receive the threaded portion of a sacral screw. In particular, traverse pin 1 may comprise a threaded, blind hole 6 shaped to receive the threaded portion of sacral screw 2, as shown in FIG. 1. Hole 6 may extend normal to the angled surface of aperture 15, which may contain an internal thread 7 for connection to sacral screw 2, as shown in FIG. 1.

Figure 3:
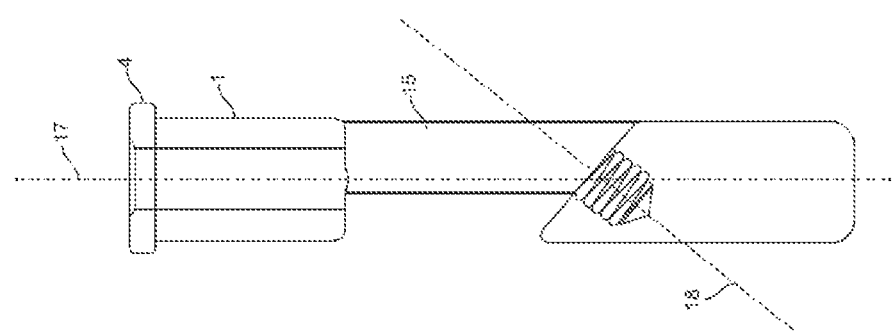
FIG. 3 is a side cross-section view of an exemplary embodiment of the transverse pin in FIG. 2.

FIG. 3 is a side cross-section view of an exemplary embodiment of the transverse pin in FIG. 2. FIG. 3 illustrates an embodiment with optional features, any of which may be optionally used or substituted with other features in other embodiments discussed herein. In particular, FIG. 3 shows a cross-sectional view of the transverse pin 1 in FIG. 2. Transverse pin comprises a predominantly triangular body of three intersecting circular regions with one flat side and head 4 of similar but larger shape than the triangular body of traverse pin 1. Additionally, FIG. 3 also illustrates longitudinal pin axis 17 and traversing thread axis 18. Thread axis 18 may be offset from pin axis 17 such that when transverse pin 1 and sacral screw 2 are attached to the plate, as shown in FIG. 1, the screw axis 8 of sacral screw 2 is coaxial with thread axis 18. Optionally, in any embodiments thread axis 18 may be in-line with a threaded, blind hole shaped to receive the threaded portion of sacral screw 2, as shown in FIG. 1. Optionally, in any embodiments transverse pin 1 may also contain an aperture with a flat upper part and angled lower surface such that traverse pin 1 has a smaller opening on one side and a larger opening on the opposite side. Transverse pin 1 may also contain a chamfered, cylindrical hole extending from head 4 to aperture 15.

Figure 4:
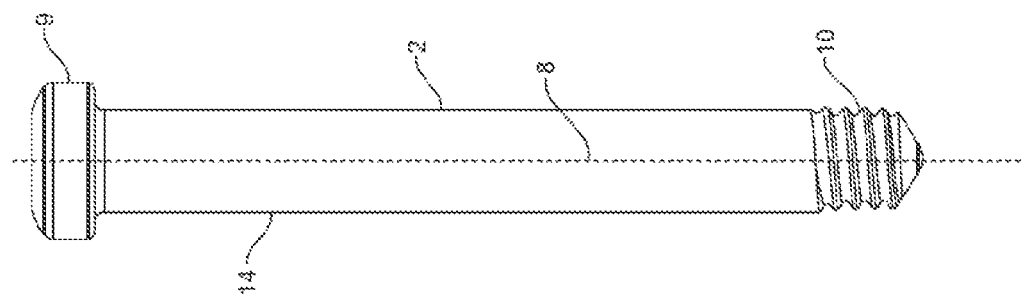
FIG. 4 is a side view of an exemplary embodiment of the sacral screw.

FIG. 4 is a side view of an exemplary embodiment of a sacral screw within an implant. FIG. 4 illustrates an embodiment with optional features, any of which may be optionally used or substituted with other features in other embodiments discussed herein. In particular, FIG. 4 is a preferred embodiment of the sacral screw 2. The sacral screw may comprise a screw axis 8 longitudinal, a cylindrical body 14, and a pan head 9 for engaging a driver tool that can rotate the screw. Optionally, in any embodiments a driver tool may be engaged by another type of head. The sacral screw may further comprise an external machine screw thread 10 along a distal portion of the length of the tubular body 14 to engage with transverse pin 1, as shown in FIG. 1.

Figure 5:
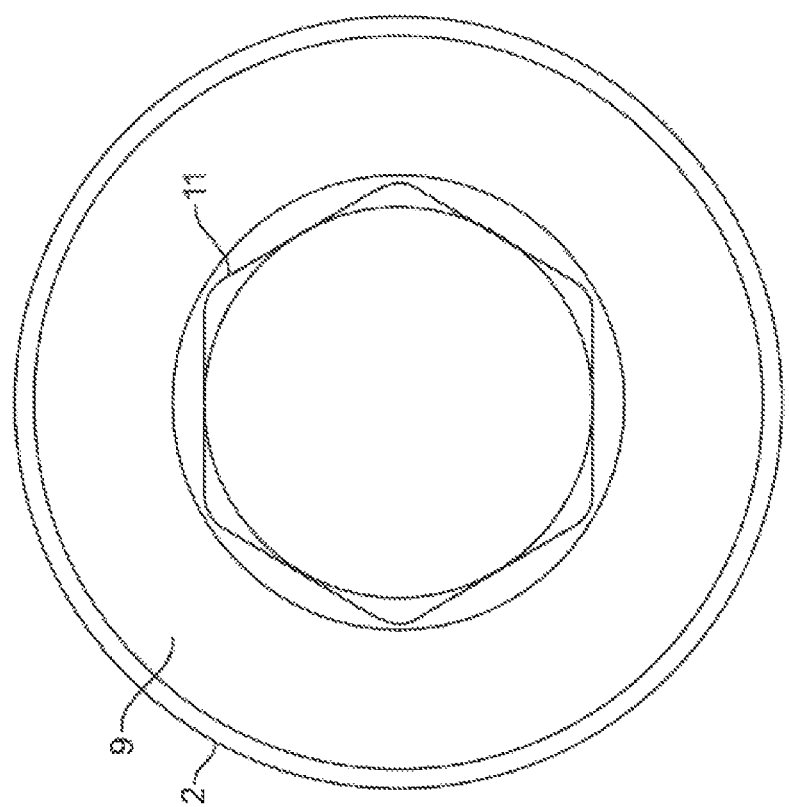
FIG. 5 is a top view of an exemplary embodiment of the sacral screw of FIG. 4.

FIG. 5 illustrates a top view of an exemplary embodiment of the sacral screw of FIG. 4. FIG. 5 illustrates an embodiment with optional features, any of which may be optionally used or substituted with other features in other embodiments discussed herein. In particular, FIG. 5 illustrates a top view of a preferred embodiment of sacral screw 2 head 9 with hexagonal recess 11 for receiving a driving tool. The diameter of cylindrical head 9 may be larger than the diameter of cylindrical body 14 as shown in FIG. 4. In examples, the diameter of cylindrical head 9 may be larger than the diameter of cylindrical body 14 so as to provide a stop to prevent driving the screw in too deep into the bone of the patient.

Figure 6:
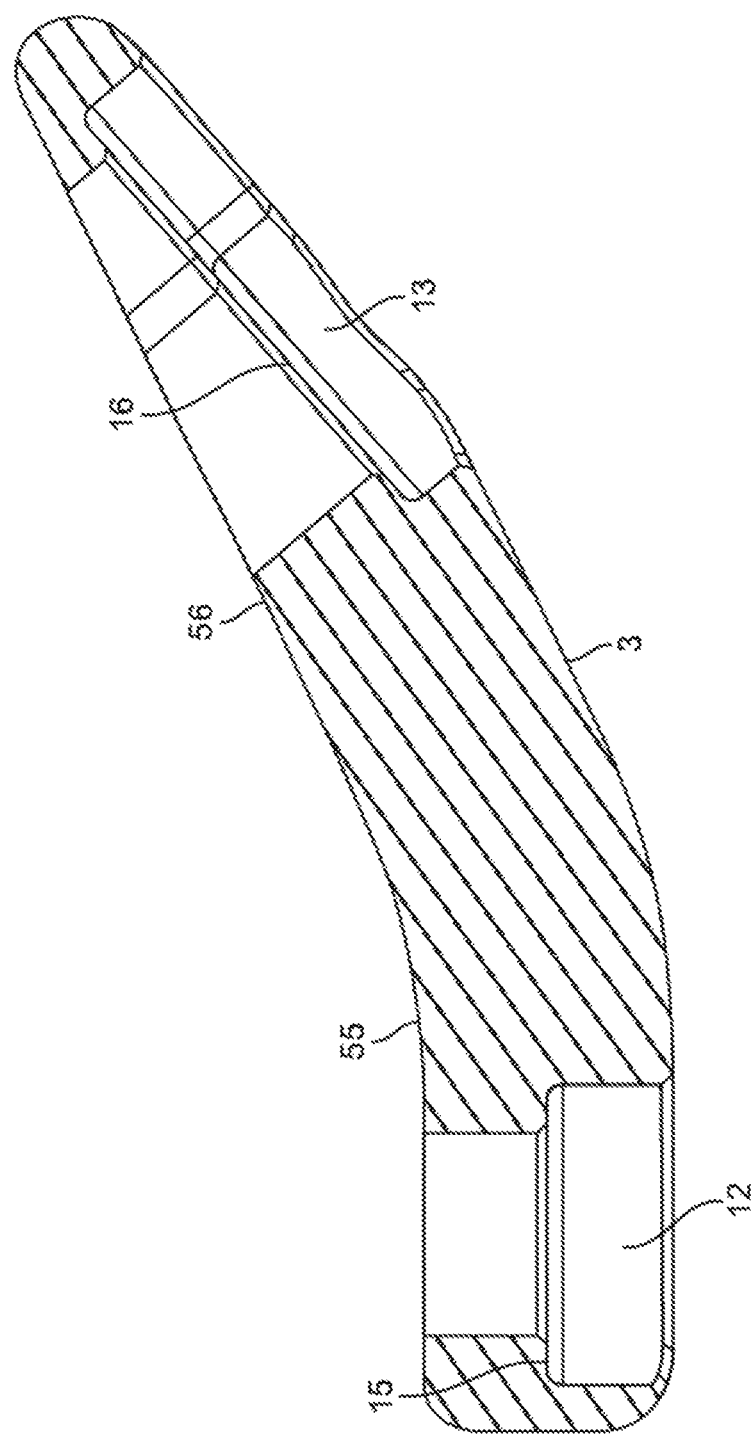
FIG. 6 is a cross-section through an exemplary embodiment of the plate.

FIG. 6 is a cross-section through an exemplary embodiment of the plate. FIG. 6 illustrates an embodiment with optional features, any of which may be optionally used or substituted with other features in other embodiments discussed herein. FIG. 6 illustrates a sacral portion and an iliac portion. Additionally, FIG. 6 is a preferred embodiment of plate 3. On one end, plate 3 comprises a cylindrical recess 12 extending through the plate with a countersink 15 for receiving sacral screw 2 and head 9, respectively. Optionally, in any embodiments cylindrical recess 12 may comprise a slotted region that may snap into place once a screw is screwed in so as to prevent a head of a sacral screw from backing out of the cylindrical recess. Optionally, in any embodiments the sacral portion may have a different shaped recess, such as a triangular recess or a square-shaped recess, among other shapes. Optionally, in any embodiments the shape of the sacral screw may match the shape of the recess within the sacral portion. Optionally, in any embodiments recesses 12 and/or 13 within a sacral portion or iliac portion, respectively, may be threaded.

In examples, plate 3 may contain on the opposite end and in another plane transverse that of the screw hole a recess 13 extending through the plate with a countersink 16 to receive transverse pin 1 and head 4, respectively. Head 9 of sacral screw 2 and head 4 of transverse pin 1 may be flush with the surface of the plate at recesses 12 and 13 respectively. Optionally, in any embodiments head 4 of transverse pin 1 may not be flush with recess 13. Optionally, in any embodiments head 9 of sacral screw 2 may not be flush with the surface of the plate at recess 12. Countersinks 15 and 16 may prevent driving sacral screw 2 and transverse pin 1, respectively, in too deep into the bone of the patient. The bone contacting the inner surface of the plate may be concave and the outer surface may be convex. More specifically, the plate may be angled 95 to 175 degrees such that surface 55 is flush with the sacrum and surface 56 is flush with the ilium allowing thread 10 of sacral screw 2 to thread into thread 7 of transverse pin 1.

Figure 7:
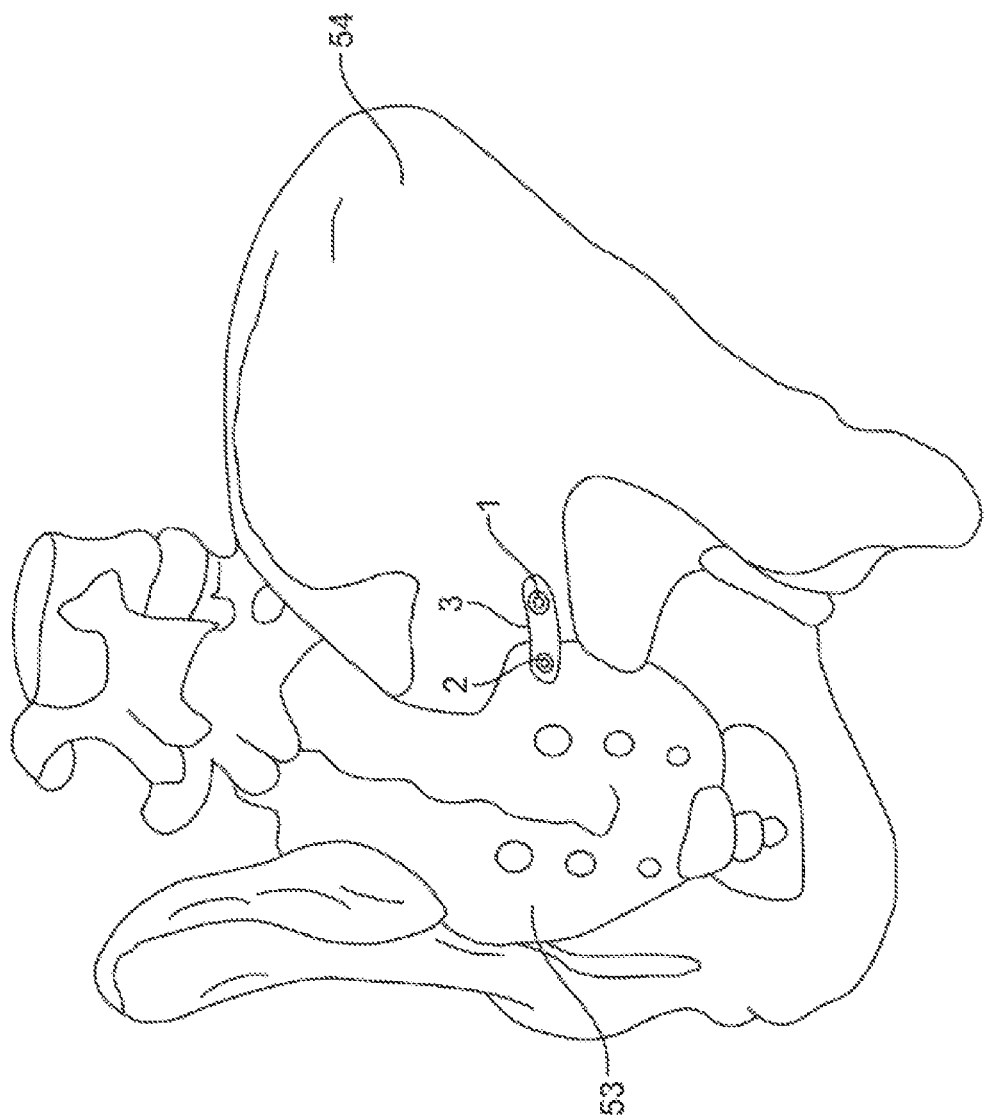
FIG. 7 is a perspective view of the embodiment shown in FIG. 1 in the sacroiliac joint space.

FIG. 7 illustrates a perspective view of the embodiment shown in FIG. 1 in the sacroiliac joint space. FIG. 7 illustrates an embodiment with optional features, any of which may be optionally used or substituted with other features in other embodiments discussed herein. In particular, FIG. 7 shows the transverse pin 1, the sacral screw 2, and the plate 3 fixating the sacrum 53 and ilium 54. In examples, the implant illustrated in FIG. 7 may be that of any implant described herein. In particular, the implant illustrated in FIG. 7 as being attached to the ilium and sacrum may be that of any implant described herein.

Figure 8:
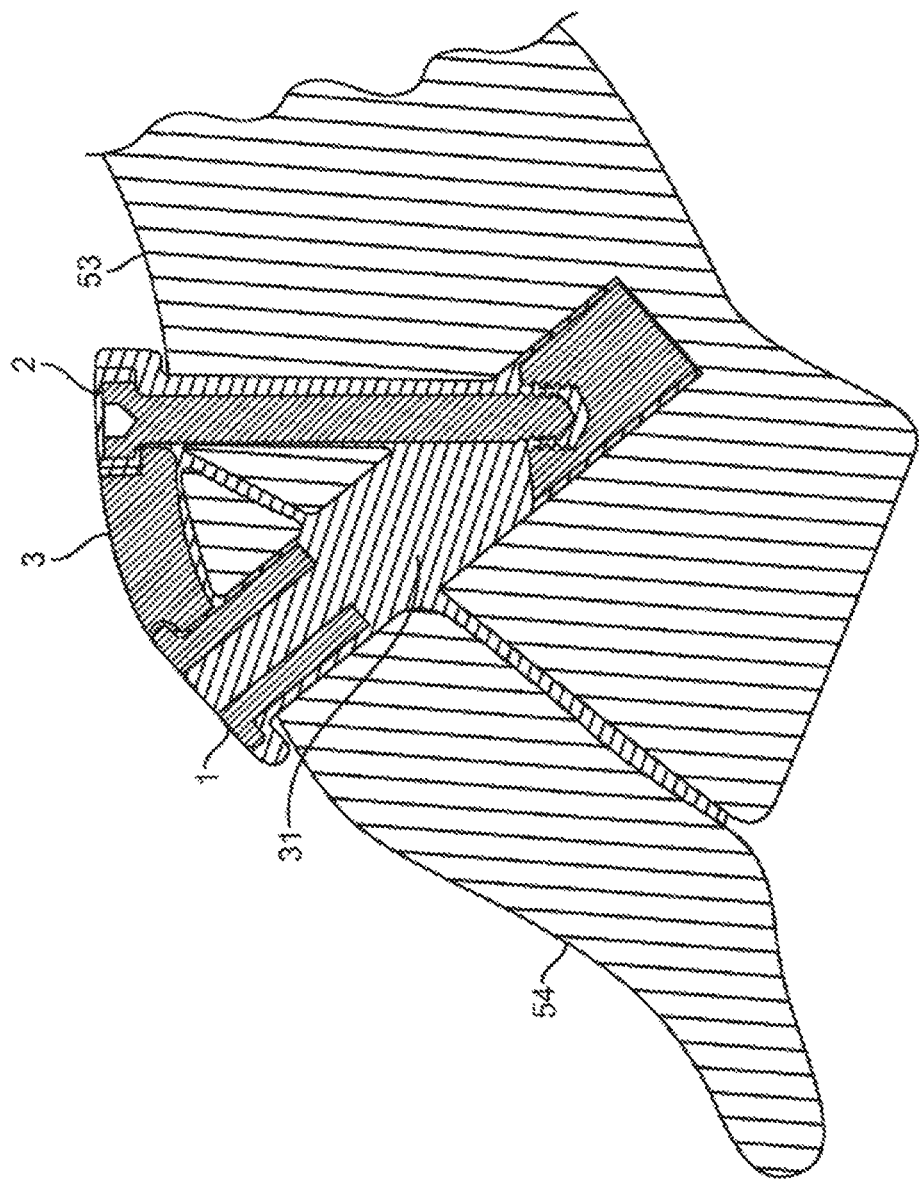
FIG. 8 is a cross-section through the embodiment in FIG. 1 in the sacroiliac joint space.

FIG. 8 illustrates a cross-section through the embodiment in FIG. 1 in the sacroiliac joint space. FIG. 8 illustrates an embodiment with optional features, any of which may be optionally used or substituted with other features in other embodiments discussed herein. FIG. 8 shows a cross section of the transverse pin 1, the sacral screw 2, and the plate 3 in the sacroiliac joint space. FIG. 8 may be viewed to highlight the surface area available for bone growth inducing material 31. Bone growth inducing material 31 may be used to enhance fusion. Plate 3 may span across sacrum 53 and ilium 54. Transverse pin 1 extends through plate 3, through ilium 54, and into sacrum 53. Sacral screw 2 may extend through plate 4, into the sacrum, and may be threaded into transverse pin 1.

Figure 9:
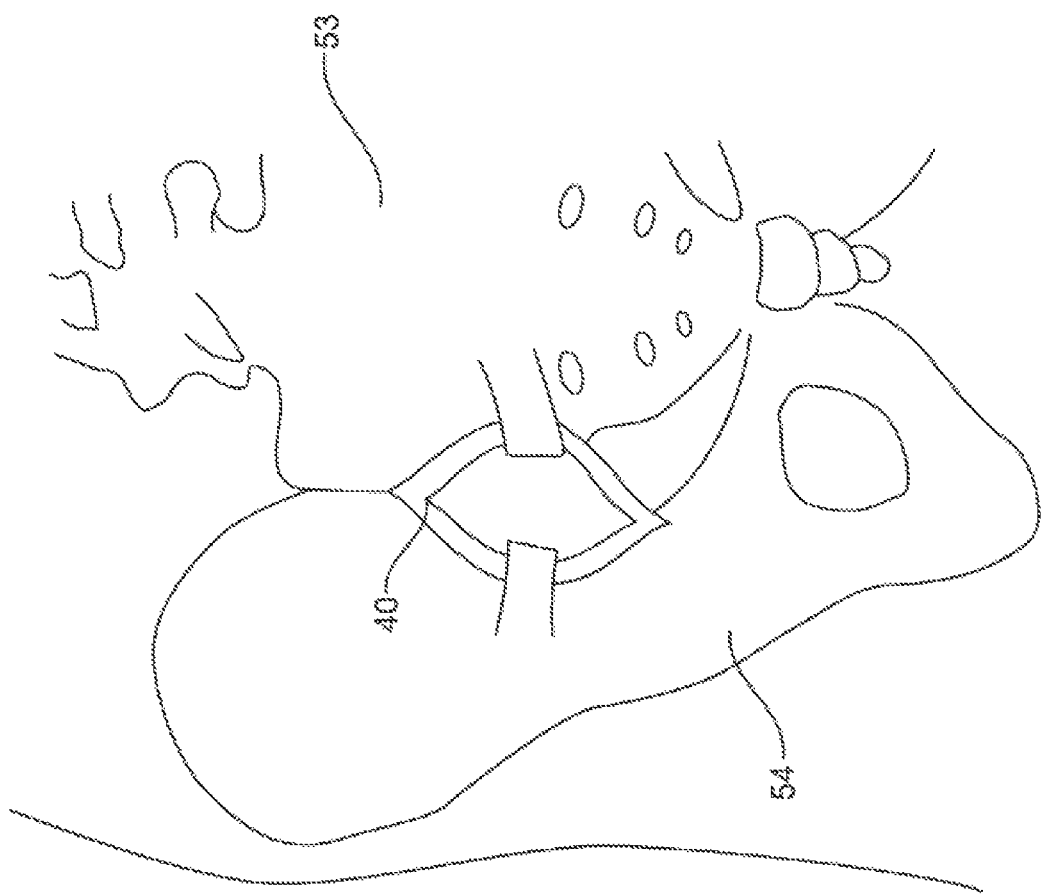
FIG. 9 is a posterior view of a patient with an incision targeting the posterior inferior end of the sacroiliac joint.
Figure 10:
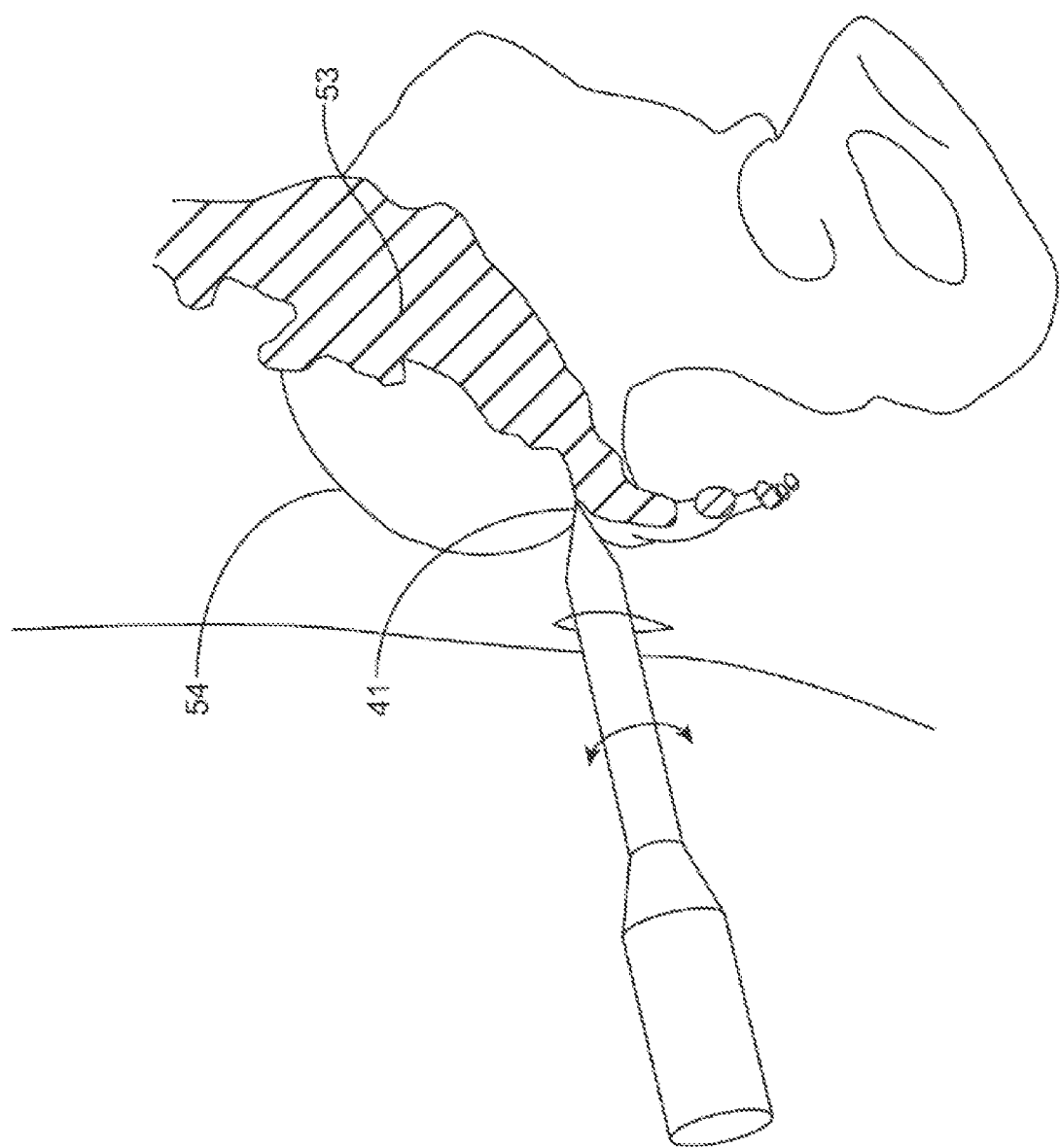
FIG. 10 is a lateral view of a patient with posterior dissection to the sacroiliac joint space.
Figure 11:
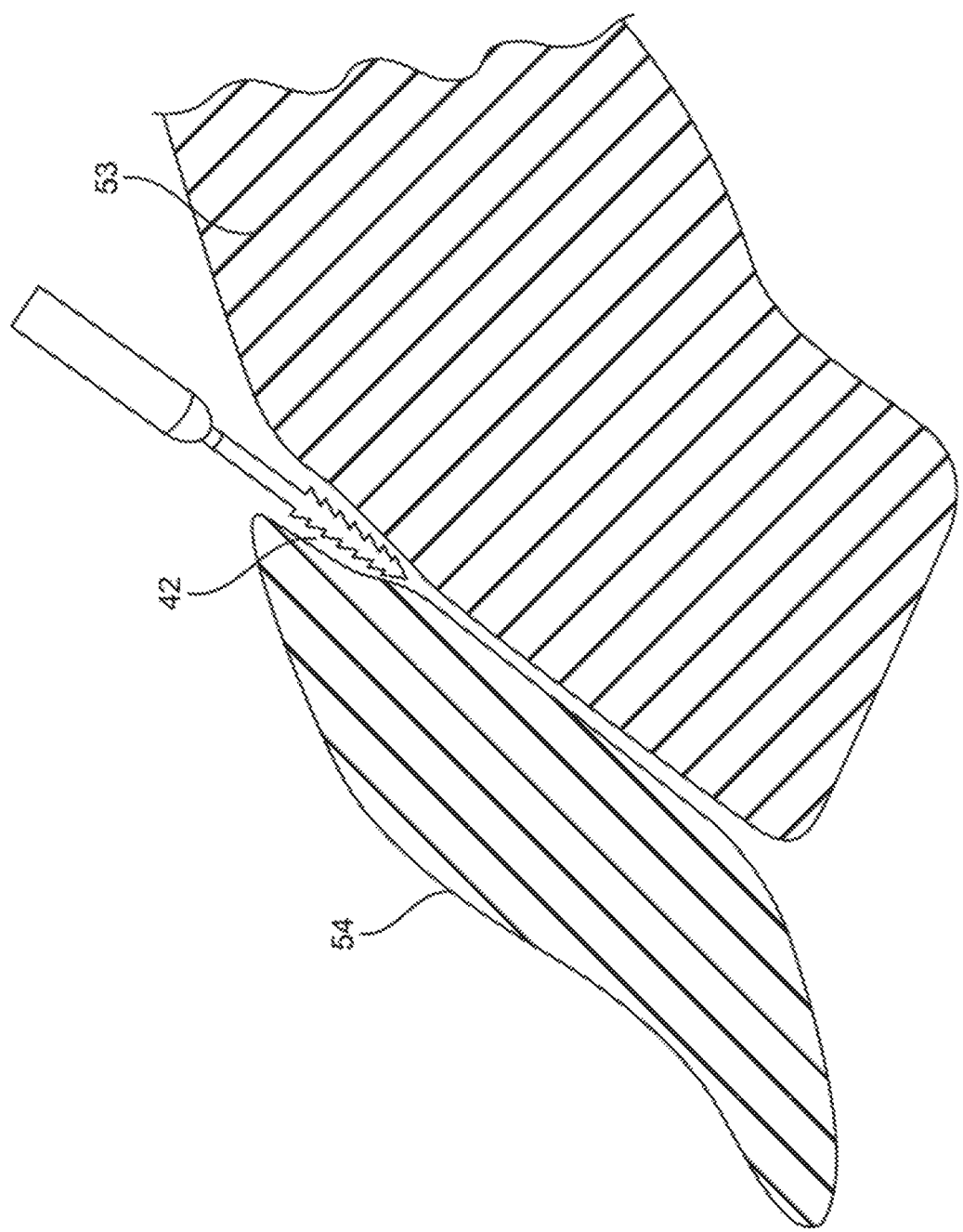
FIG. 11 is a lateral cross-sectional view of decortication of the sacroiliac joint space.

FIGS. 9-11 illustrates embodiments for delivering an implant, such as in FIGS. 1-8 above, into a sacroiliac joint space of a patient. FIG. 9 illustrates a posterior view of a patient with an incision targeting the posterior inferior end of the sacroiliac joint. FIG. 9 illustrates an embodiment with optional features, any of which may be optionally used or substituted with other features in other embodiments discussed herein. FIG. 9 shows the location of an incision 40 at the posterior inferior end of the sacroiliac joint. The sacroiliac joint is illustrated as having a sacro component 53 and an iliac component 54.

FIG. 10 is a lateral view of a patient with posterior dissection to the sacroiliac joint space. FIG. 10 illustrates an embodiment with optional features, any of which may be optionally used or substituted with other features in other embodiments discussed herein. FIG. 10 illustrates dissection 41 down to the posterior inferior end of the sacroiliac joint space using a standard cobb-like instrument with a sweeping motion in the same plane as the joint. Optionally, in any embodiments an alternative instrument for dissection 41 may be conducted using FIG. 11 is a lateral cross-sectional view of decortication of the sacroiliac joint space. FIG. 11 illustrates an embodiment with optional features, any of which may be optionally used or substituted with other features in other embodiments discussed herein. FIG. 11 illustrates decortication 42 of the sacroiliac joint space using a rectangular rasp-like instrument to remove outer cortical bone from both sacrum and ilium with a reciprocating in/out motion.

Figure 12:
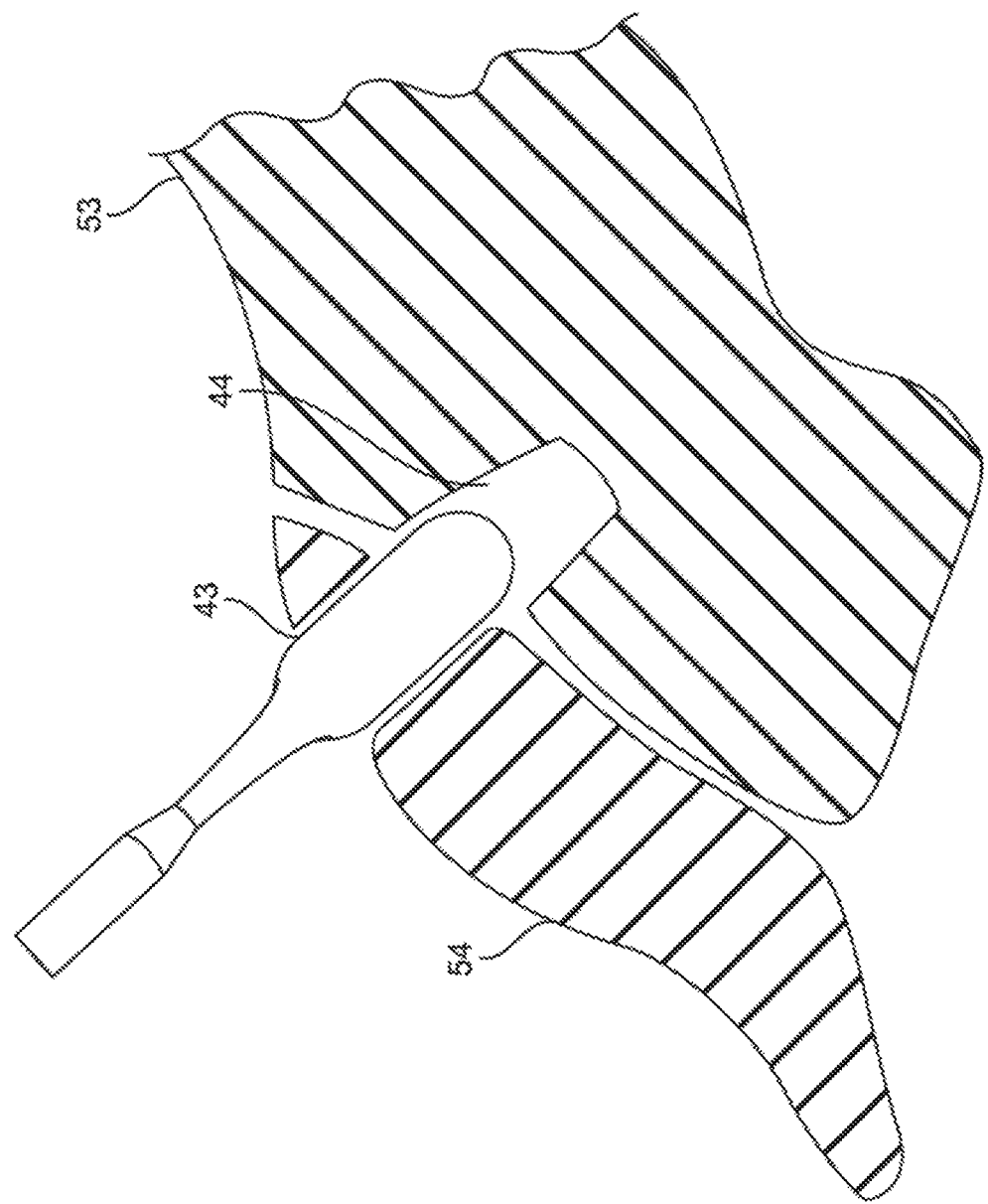
FIG. 12 is a lateral cross-sectional view of a broach creating a void across the sacroiliac joint space shaped to receive a transverse pin.

FIG. 12 illustrates the use of a broach 43 to create a void 44 through the ilium 54 and into the sacrum 53 that is shaped to receive transverse pin 1. FIG. 12 illustrates an embodiment with optional features, any of which may be optionally used or substituted with other features in other embodiments discussed herein. A mallet may be used to hammer on the back end of the broach to advance the broach for void creation. Optionally, in any embodiments the broach may include depth markings to indicate when the broach is at the proper depth and thereby when the void length matches the length of the intended transverse pin. Optionally, in any embodiments the void matches the shape and length of the pin. In these examples, the amount of material that is removed is also based on the shape and length of the pin. Optionally, in any embodiments a void is created that is greater than the shape and length of the pin. Optionally, in any embodiments excess void area is filled in bone growth inducing material. Optionally, in any embodiments void 44 is generated after decortication. As seen in FIG. 12, the space between the sacrum and ilium is larger in the decorticated section that was shown in FIG. 11.

Figure 13:
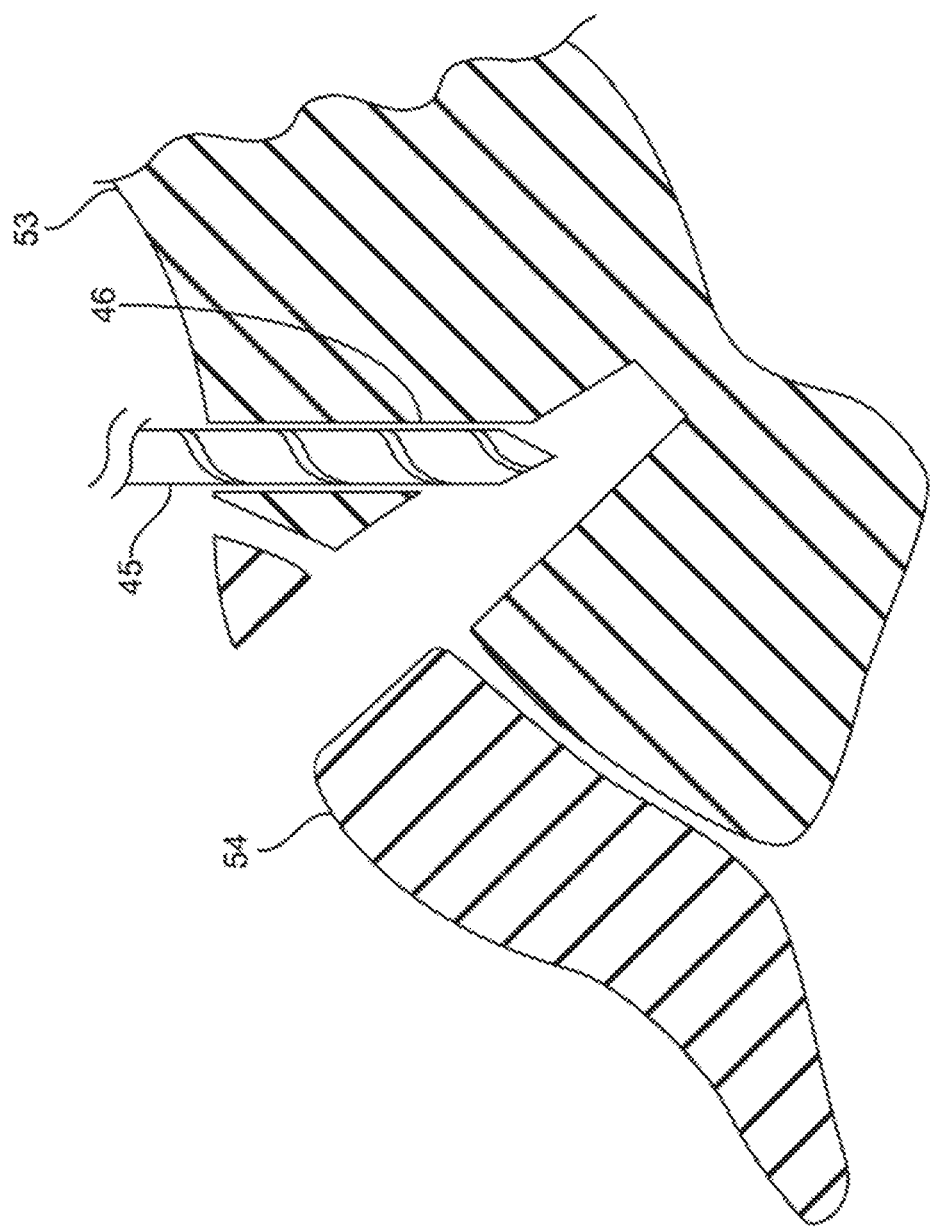
FIG. 13 is a lateral cross-sectional view of a drill creating a void through the sacrum shaped to receive a sacral screw.

FIG. 13 illustrates the use of a drill 45 to create a void 46 through the sacrum 53 that is shaped and located to receive sacral screw 2. FIG. 13 illustrates an embodiment with optional features, any of which may be optionally used or substituted with other features in other embodiments discussed herein. The diameter of drill 45 is preferably sized to match the minor diameter of the threaded shaft of screw and may include depth markings to indicate what length screw to choose.

Figure 14:
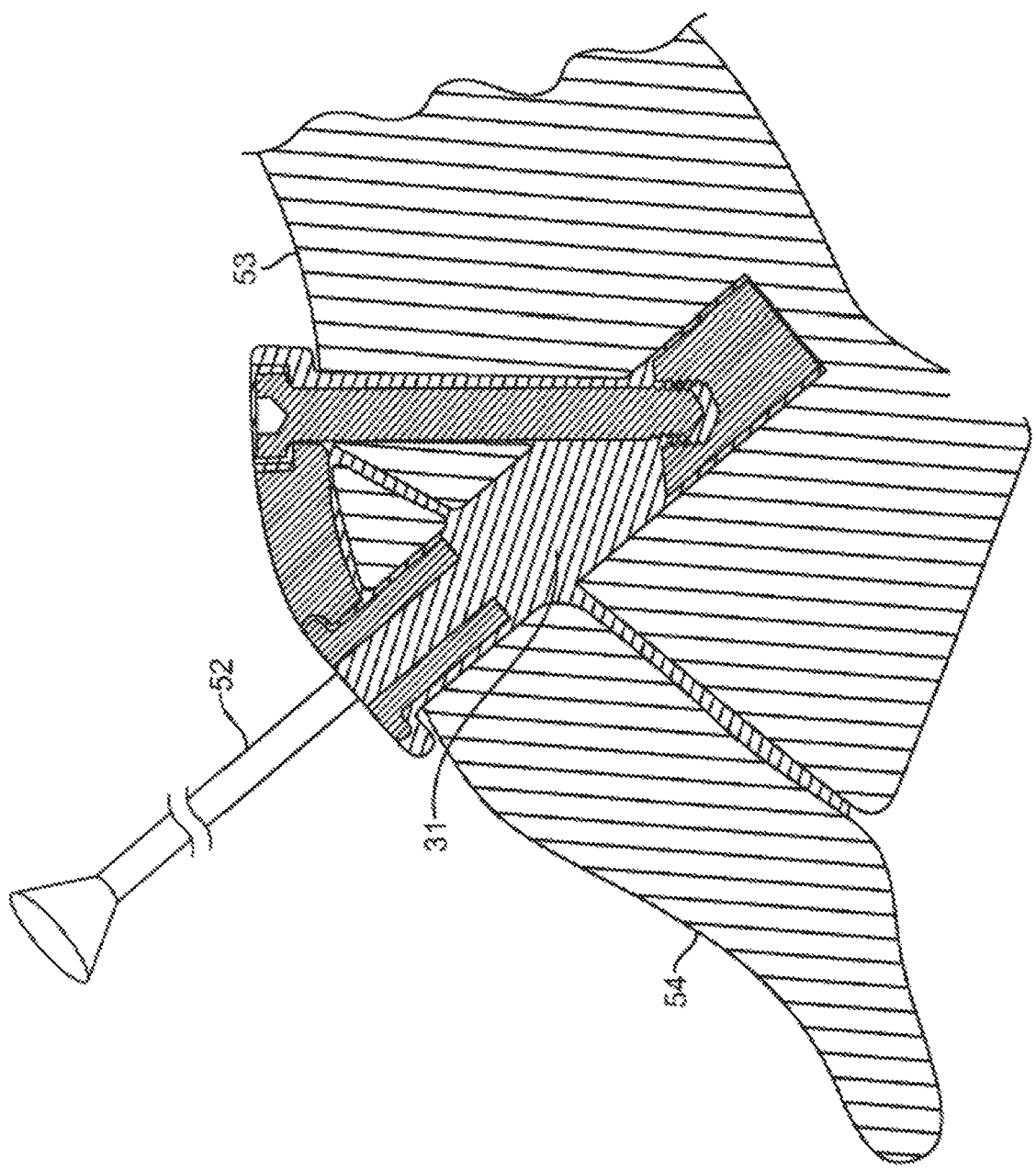
FIG. 14 is a cross-sectional view of the implant being packed with bone growth inducing material after insertion in the sacroiliac joint space.

FIG. 14 illustrates a bone growth inducing material delivery device 52 comprising a conical funnel and long tube for introducing bone growth inducing material 31. FIG. 14 illustrates an embodiment with optional features, any of which may be optionally used or substituted with other features in other embodiments discussed herein. Additional examples may include a syringe injection for the bone growth inducing material, hand delivery of the bone growth inducing material, or other examples of providing the bone growth inducing material to the joint space. Examples of bone growth inducing material may include autograft, allograft, medical adhesives, bonding cements, and/or bone healing substances. Optionally, in any embodiments bone growth inducing material may be provided into the joint space through the transverse pin 1 after implant insertion in the sacroiliac joint space. Bone growth inducing material may be inserted into the funnel. Optionally, in any embodiments a plunging tool such as a cylindrical rod may be used to push the bone growth inducing material through the long tube and into the hole in the pin that extends from the pin head to the slotted region. In this way, the slotted region that crosses the sacroiliac joint may be filled with bone growth inducing material.

Figure 15:
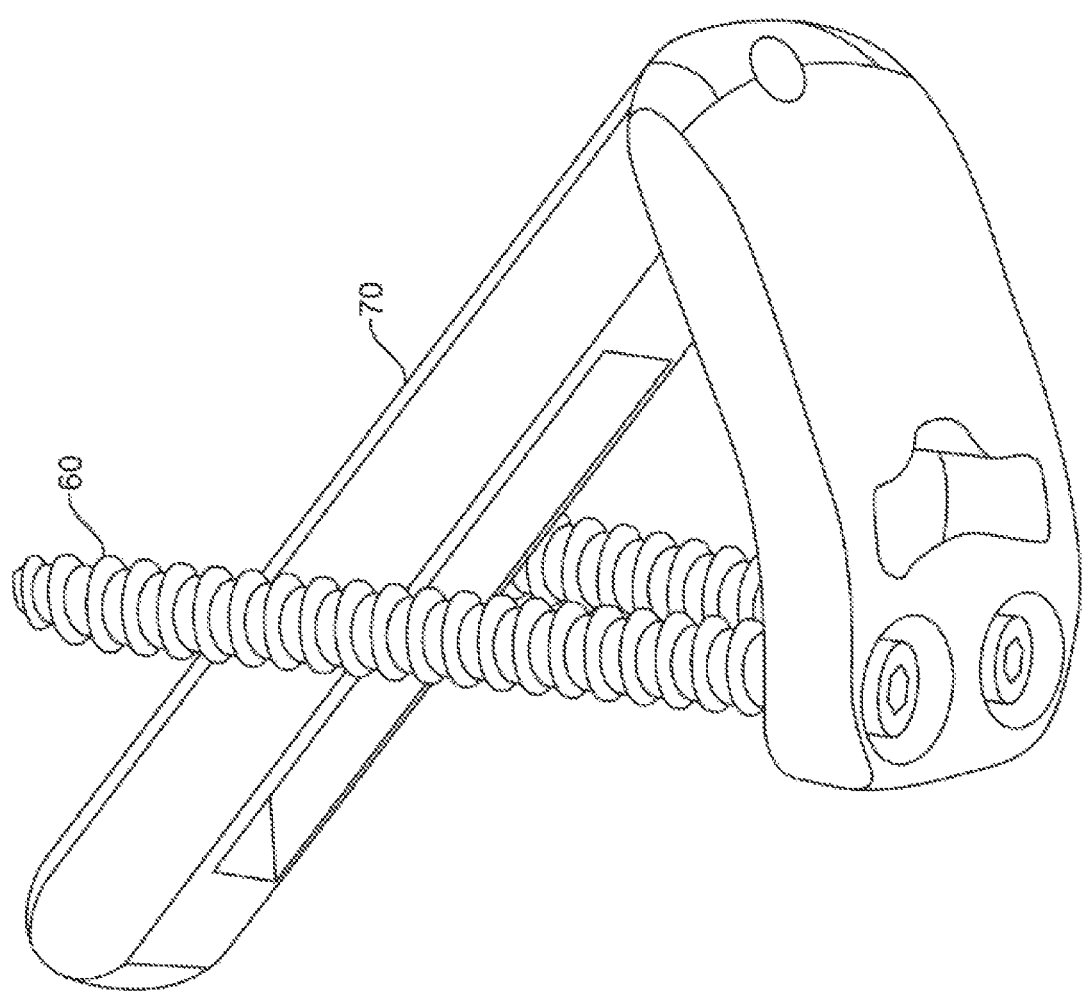
FIG. 15 is a perspective view of the implant comprising a plate, pin, and two sacral screws.
Figure 16B:
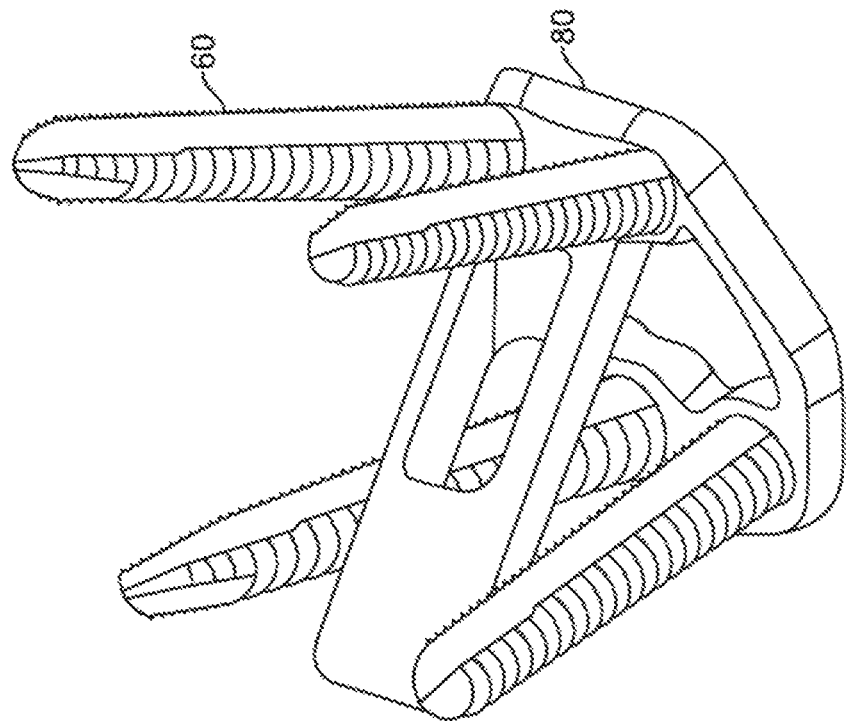
FIG. 16B is a perspective view of the implant comprising a plate, pin, two sacral screws, and two iliac screws.
Figure 16A:
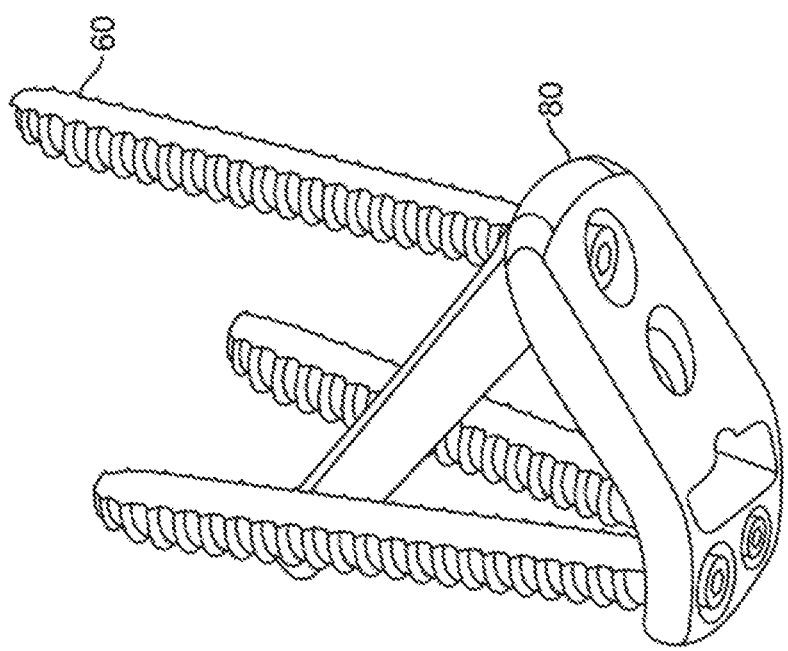
FIG. 16A is a perspective view of the implant comprising a plate, pin, two sacral screws, and one iliac screw.

FIG. 15 shows a preferred embodiment of the implant where a one-piece or integral/monolithic plate/pin 70 and two bone screws 60 in the sacrum may immobilize the sacroiliac joint. FIG. 15 illustrates an embodiment with optional features, any of which may be optionally used or substituted with other features in other embodiments discussed herein. The two bone screws 60 as provided in FIG. 15 are positioned so as to straddle the pin component of plate/pin 70. Optionally, in any embodiments the bone screws 60 may not touch the pin component of plate/pin 70. Optionally, in any embodiments the bone screws 60 may be non-parallel. The plate component and pin component of plate/pin 70 may form an L-shaped or J-shaped bracket having an elongated linear section extending along an axis, and a shorter section coupled to one end of the elongated linear section and extending transverse to the axis. Optionally, in any embodiments the elongated linear section and the shorter section may be integrally formed. Optionally, in any embodiments the elongated linear section and the shorter section may be coupleable together. The angle between the shorter section and the elongated linear section may preferably ranges from 15 to 75 degrees. The short section, which may also be known as a plate component, may include one or more holes sized to receive a bone screw for securing the implant to the sacrum. The elongated linear section, which may also be known as a pin component, may form a pin that traverses through the ilium and sacrum. Optionally, in any embodiments the pin component that is formed may be sized such that it does not contact the bone screw(s). Additionally, the pin component may have a rectangular slotted region extending through the elongated linear section in which bone graft material may be disposed for facilitating fusion FIGS. 16A and 16B are similar to FIG. 15 except that FIGS. 16A and 16B also comprise one or more bone screws to be inserted into the ilium. Similar to FIG. 15, FIGS. 16A and 16B include a rectangular aperture within a pin portion of plate/pin 80 that may be used to deliver bone growth inducing material. Additionally, similar to FIG. 15, FIGS. 16A and 16B include an irregular aperture within a plate portion of plate/pin 80 that may be used to deliver bone growth inducing material. In particular, FIGS. 16A and 16B show a preferred embodiment of the implant where a one-piece integral or monolithic plate/pin 80, bone screws 60 in the sacrum, and one or more bone screws in the ilium immobilize the sacroiliac joint. FIG. 16A illustrates a monolithic plate/pin 80 having two bone screws to be inserted into the sacrum and one bone screw to be inserted into the ilium. FIG. 16A illustrates an embodiment with optional features, any of which may be optionally used or substituted with other features in other embodiments discussed herein. FIG. 16B illustrates a monolithic plate/pin 80 having two bone screws to be inserted in to the sacrum and two bone screws to be inserted into the ilium. FIG. 16B illustrates an embodiment with optional features, any of which may be optionally used or substituted with other features in other embodiments discussed herein. In examples, an implant may have more than two bone screws to be inserted into the sacrum. In examples, an implant may have more than two bone screws inserted into the sacrum. The holes for receiving the screws may be angled relative to one another so that the screws are also angled relative to one another and so that the screws enter the bone at a desired angle. In embodiments, the angles may be any angle that matches the patient's anatomy. In preferred embodiments the relative angle between any two adjacent iliac or sacral screws may preferably diverge 5-30 degrees, more preferably 10-20 degrees, and more preferably diverge about 15 degrees. In examples, two or more bone screws may be non-parallel with respect to one another.

In examples, the plate component and pin component of plate/pin 80 may form an L-shaped or J-shaped bracket having an elongated rectangular or linear section extending along an axis, and a shorter section coupled to one end of the elongated linear section and extending transverse to the axis. The short section may include one or more holes sized to receive a bone screw for securing the implant to the sacrum. The elongated linear section may form a pin that traverses through the iliac and sacrum, and a distal portion of the elongated linear portion may be beveled or otherwise shaped to have a sharp point to help penetrate bone. It may have a rectangular slotted region extending through the elongated linear section in which bone graft material may be disposed for facilitating fusion. As seen in FIG. 16A, the two sacral screws may be placed through two holes on the short section of the plate and into the sacrum and preferably disposed on either side of and not in contact with the elongated linear section. Also as seen in FIG. 16A, one iliac screw may be placed through a hole. The hole may be centrally located through the junction between the short section of the plate and the elongated linear section. The iliac screw may be placed through the hole into the ilium. As seen in FIG. 16B, two sacral screws may be placed through two holes on the short section of the plate and into the sacrum. The two sacral screws may be preferably disposed on either side of, and not in contact with, the elongated linear section. As also seen in FIG. 16B, two iliac screws may be placed through two holes, the holes located through the junction between the short section of the plate and the elongated linear section, and into the ilium. Optionally, in any embodiments the shorter sacral portion may be flat and planar. Optionally, in any embodiments the shorter sacral portion may have an arcuate surface that matches the contours of the sacrum. Optionally, in any embodiments the screw heads may preferably fit into the holes such that the screw heads are flush. Optionally, in any embodiments the screw heads may fit below the outer surface of the plate.

FIGS. 17A-17D show a preferred embodiment of the bone screw 60 that may be used with any of the implants described herein. FIG. 17A illustrates a perspective view of an exemplary embodiment of a bone screw. FIG. 17A illustrates an embodiment with optional features, any of which may be optionally used or substituted with other features in other embodiments discussed herein. FIG. 17B illustrates a cross-section view of the embodiment in FIG. 17A. FIG. 17B illustrates an embodiment with optional features, any of which may be optionally used or substituted with other features in other embodiments discussed herein. FIG. 17C illustrates a front view of the embodiment in FIG. 17A. FIG. 17C illustrates an embodiment with optional features, any of which may be optionally used or substituted with other features in other embodiments discussed herein. FIG. 17D illustrates a top view of the embodiment in FIG. 17B. FIG. 17D illustrates an embodiment with optional features, any of which may be optionally used or substituted with other features in other embodiments discussed herein.

The bone screw may contain an externally threaded, cylindrical head 62 that extends along the same axis as an elongated, externally threaded, cylindrical shaft 63 of smaller diameter. Threaded head 62 may engage with internally threaded holes 78 or 81 of plate/pin 70 or plate/pin 80 as shown in FIGS. 15 and 16, respectively. In examples, the threaded head may engage with internally threaded holes of any plate/pin embodiment disclosed herein. Threaded shaft 63 may be disposed through the plate/pin along the axis of the threaded holes. In examples, threaded shaft 63 may be preferably disposed along the majority/entire length of the screw shaft, may engage with bone, and may thereby secure the implant to the sacrum or ilium. Threaded shaft 63 may also contain cutting flute 64 adjacent the distal end and a tapered tip 66 at the distal portion thereof, to aid in insertion, both of which extend along the screw's axis. Threaded head 62 has larger diameter than screw shaft and may also contain countersunk hex socket 61 and internal threaded hole 65 to engage with an insertion tool, again extending along its axis. Bone screw 60 may vary in length 10 to 100 mm and may vary in diameter 4 to 12 mm, although these dimensions are not limiting and may be adjusted based on the patient's anatomy being treated.

FIGS. 18A-18D show a preferred embodiment of plate/pin 70 which contains an oval, elongated linear section or "pin member" 72 extending along an axis and a shorter rectangular section or "plate member" 71 coupled to one end of the elongated linear section and extending transverse to the longitudinal axis of the elongated linear section. FIG. 18A is a perspective view of an exemplary embodiment of the plate/pin. FIG. 18A illustrates an embodiment with optional features, any of which may be optionally used or substituted with other features in other embodiments discussed herein. FIG. 18B is a cross-sectional front view of the embodiment in FIG. 18A. FIG. 18B illustrates an embodiment with optional features, any of which may be optionally used or substituted with other features in other embodiments discussed herein. FIG. 18C is a cross-sectional side view of the embodiment in FIG. 18A. FIG. 18C illustrates an embodiment with optional features, any of which may be optionally used or substituted with other features in other embodiments discussed herein. FIG. 18D is a top view of the plate/pin shown in FIG. 18A. FIG. 18D illustrates an embodiment with optional features, any of which may be optionally used or substituted with other features in other embodiments discussed herein.

The pin member and the plate member may optionally take the same form as described in other embodiments, such as in FIG. 15 or 16. Plate member 71 may contain a sacrum contacting surface 73 and ilium contacting surface 74, the angle (indicated by a dotted curve in FIG. 18B) between which may vary preferably 95 to 175 degrees, although other angles are possible depending on the patient's anatomy. Plate member 71 may also contain a slotted region 76 which may be cruciform shaped. In additional examples, the slotted region may be another desired shape such as round, rectangular, triangular, oval, as well as other examples. The slotted region may allow the surgeon to see the joint and pack additional bone graft material through it if desired. Plate member 71 may also contain a hex socket or similar feature 79 and threaded hole 78 which extend along or substantially parallel to the axis of the pin member and engage with an impaction tool that helps drive the pin into bone. Plate 71 also contains diverging, preferably 5 to 30 degrees, internally chamfered and threaded sacral screws holes 77 with unthreaded, cylindrical section 82 adjacent to the bone contacting surface of the plate member to prevent bone screws 60 from translating through the plate. Pin member 72 traverses the sacroiliac joint, first passing through the ilium, then crossing the joint, and finally entering the sacrum, as shown in the implantation position in FIG. 20. Pin member 72 varies in length preferably 20 to 60 mm and may contain a rectangular slotted region 75 extending through the pin member in which bone graft material may be disposed for facilitating fusion. Other aspects of the implant may generally take the same form as other embodiments described herein.

Figure 19:
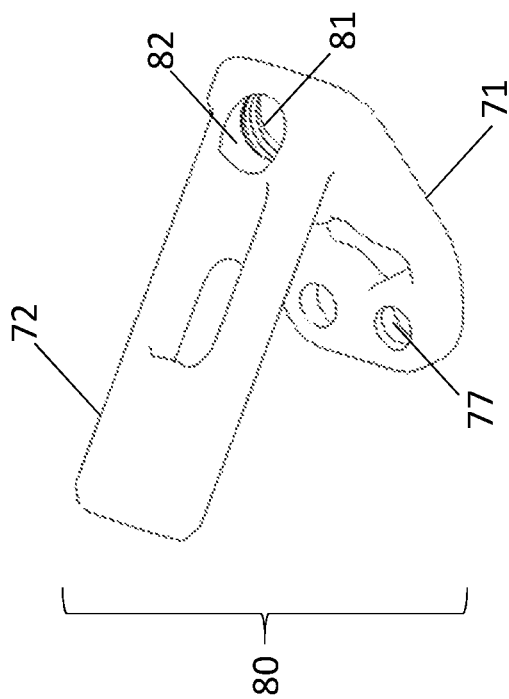
FIG. 19 is a perspective view of an exemplary embodiment of a plate/pin.

FIG. 19 shows a preferred embodiment of plate/pin 80 which contains an elongated linear section or "pin member" 72 extending along an axis, and a shorter section or "plate member" 71 coupled to one end of the elongated linear section and extending transverse to the axis. FIG. 19 illustrates an embodiment with optional features, any of which may be optionally used or substituted with other features in other embodiments discussed herein. Plate/pin 80 also contains internally threaded bone screw hole(s) 77 and 81 to receive bone screw(s) 60 to engage with the sacrum and ilium, respectively. Bone screw hole(s) 81 also features an unthreaded cylindrical section 82 adjacent to the bone contacting surface of the plate/pin to prevent bone screw(s) 60 from translating through the device.

Figure 20:
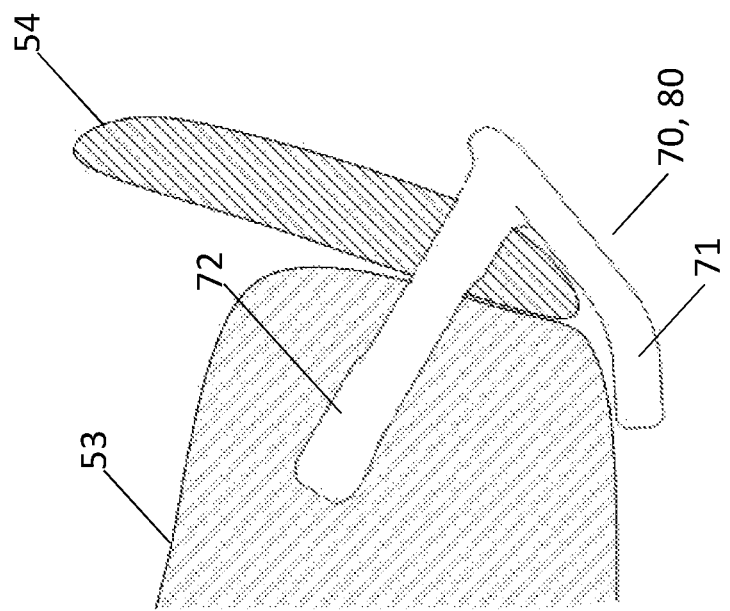
FIG. 20 illustrates the plate/pin implantation position on a cross-section of the sacroiliac joint.

FIG. 20 illustrates the plate/pin 70 or 80 implantation position on a cross-section of the sacrum 53 and ilium 54. FIG. 20 illustrates an embodiment with optional features, any of which may be optionally used or substituted with other features in other embodiments discussed herein. Here the elongate linear portion, or pin 72, passes through the sacrum and ilium and the shorter portion, or plate 71, has an arcuate surface that allows the shorter portion to conform to the sacrum and ilium where it may be screwed into position as described in other figures. The implant comprising plate/pin 70 or 80 also includes bone screw(s) (not shown) that pass into the sacrum and bone screw(s) (not shown) that pass into the ilium. Examples of bone screws inserted into a plate/pin, such as plate/pin 70 or 80, are provided throughout the disclosure. Embodiments of bone screws as described herein may be used in accordance with plate/pin 70 or 80, as well as other implant configurations.

Figure 21:
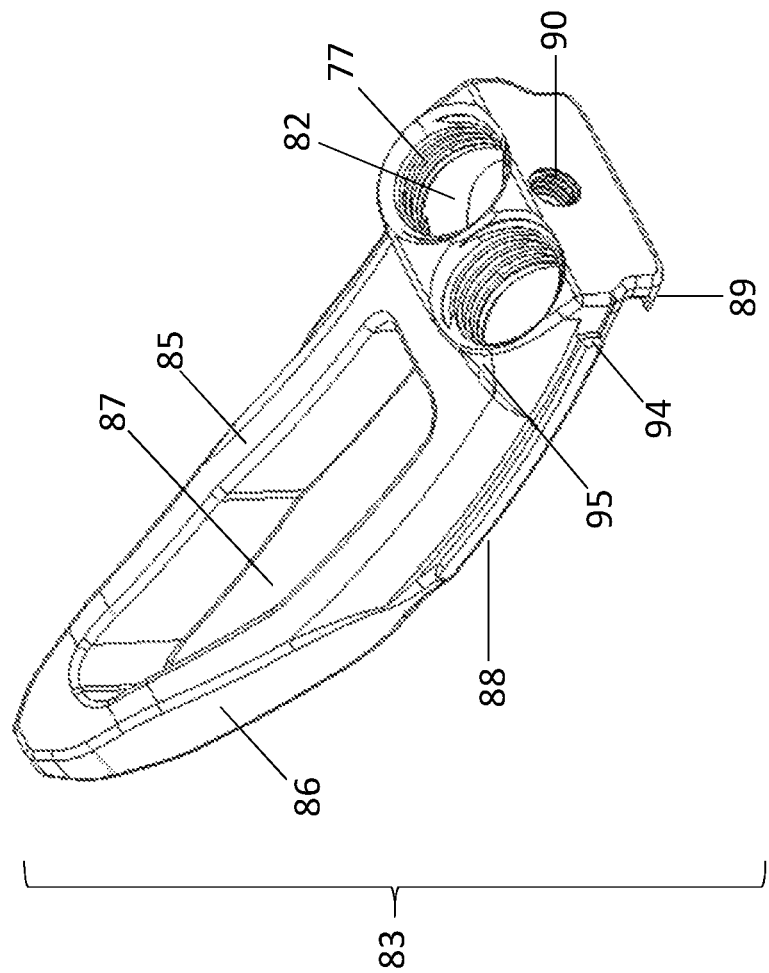
FIG. 21 is a perspective view of another exemplary embodiment of a transverse pin.

FIG. 21 is a perspective view of another exemplary embodiment of a transverse pin 83 having a curved oval main body 85. FIG. 21 illustrates an embodiment with optional features, any of which may be optionally used or substituted with other features in other embodiments discussed herein. Curved main body 85 has a tapered end 86 to allow for placement of transverse pin 83 between and not in contact with two bone screws in the sacrum and extension 95 traverse to the main body. Extension 95 contains two partially threaded diverging bone screw holes 77 with unthreaded section 82 to receive and act as a stop for bone screws to be placed through transverse pin 83 and into the ilium. Optionally, in any embodiments different inserter features may be provided for inserting bone screws. Extension 95 also contains threaded blind hole 90. In examples, blind hole 98 may be used to engage with an inserter tool. Additionally, extension 95 also comprises overhang 89. Overhang 89 may hook around a corresponding pocket in plate 84 in FIG. 22 so as to stop from driving transverse pin 83 in too deep. In examples, overhang 89 may act as a hard stop during insertion. In examples, overhang 89 may help prevent rotation of the pin relative to the plate. Transverse pin 83 may also contain two rectangular rails 88 extending along the narrow ends 86 of oval main body 85. Ends 86 of oval main body 85 may be tapered. Rectangular rails 88 may follow the curve partially along extension 95. Rails, such as rectangular rails 88, may act as a guide for transverse pin 83 implantation. In examples, rails may act as a guide for inserting transverse pin 83 during implantation. Rails may contain flat end 94 that, upon engagement with plate 84 in FIG. 22, may prevent transverse pin 83 from backing out. Transverse pin 83 also contains aperture 87. Aperture 87 extends through transverse pin 83 and, as illustrated in FIG. 21, has a generally rectangular portion that tapers towards an end. In examples, aperture 87 may approximate the shape of main body 85 and taper 86. Optionally, in any embodiments aperture 87 may be packed with bone growth inducing material. Optionally, in any embodiments aperture 87 may be packed with bone growth inducing material prior to implantation. Optionally, in any embodiments bone growth inducing material that is provided to a sacroiliac joint gap, or an adjacent area, may be provided through aperture 87. Examples of bone growth inducing material may include biologics, agents, medical adhesives, bonding cements and/or bone healing substances. In examples, a curved transverse pin, such as pin 83 illustrated in FIG. 21, may be shaped for placement through the ilium, through the sacroiliac joint space, and into the sacrum.

Optionally, in any embodiments a transverse pin, such as transverse pin 83, may be between 20 mm-60 mm in length. Optionally, in any embodiments a transverse pin may be less than 20 mm, 20 mm, 25 mm, 30 mm, 35 mm, 40 mm, 45 mm, 50 mm, 55 mm, 60 mm, or more than 60 mm. In examples, pin lengths may vary. In examples, pins described throughout this disclosure may vary in length. Optionally, in any embodiments a pin may vary in length based on anatomy of a patient. In examples, bone screws may have a divergence between 0 degrees-30 degrees. Optionally, in any embodiments bone screws may have a divergence of 0 degrees, 5 degrees, 10 degrees, 15 degrees, 20 degrees, 25 degrees, 30 degrees, or more than 30 degrees.

Figure 22:
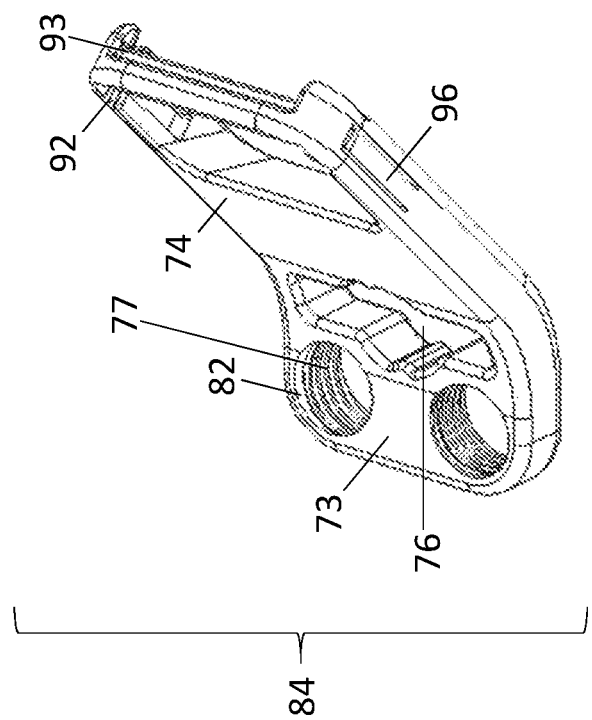
FIG. 22 is a perspective view of another exemplary embodiment of a plate.

FIG. 22 is a perspective view of another exemplary embodiment of a plate 84 which is rectangular in shape with sacrum contacting surface 73 and ilium contacting surface 74, the angle between which may vary preferably 95 to 175 degrees, although other angles are possible depending on the patient's anatomy. FIG. 22 illustrates an embodiment with optional features, any of which may be optionally used or substituted with other features in other embodiments discussed herein. Plate 84 also contains a slotted region 76 which may be cruciform shaped or any other desired shape such as round, rectangular, triangular, oval, etc., and allows the surgeon to see the joint, aiding in proper plate placement, and pack additional bone graft material through it if desired. Plate 84 also contains diverging, preferably 5 to 30 degrees, internally chamfered and threaded sacral screws holes 77 with unthreaded, cylindrical section 82 adjacent to the bone contacting surface of the plate member to prevent bone screws 60 from translating through the plate. Plate 84 also contains two slots 92 traverse to the iliac contact surface of the plate and pocket 93 partially extending along the lateral outer edge of plate 84. Slots 92 and pocket 93 may be shaped to receive rails 88 and overhang 89, respectively, of transverse pin 83 in FIG. 21. Plate 84 also contains two arms 96 on either side of the iliac side of the plate, with the long edge parallel to ilium contact surface 74 that may flare outward during transverse pin 83 insertion and return to neutral position (e.g., that shown in FIG. 22) once transverse pin 83 is fully seated.

Figure 23C:
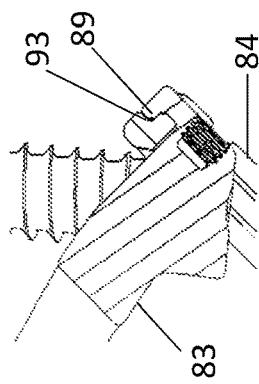
FIG. 23C is a cross-sectional front view of engagement between the transverse pin and plate of FIGS. 21 and 22, respectively.
Figure 23D:
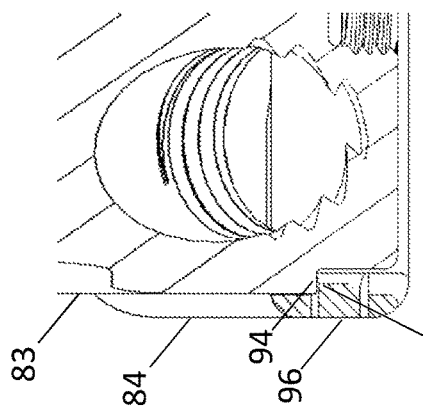
FIG. 23D is a cross-sectional side view of engagement between the transverse pin and plate of FIGS. 21 and 22, respectively.
Figure 23B:
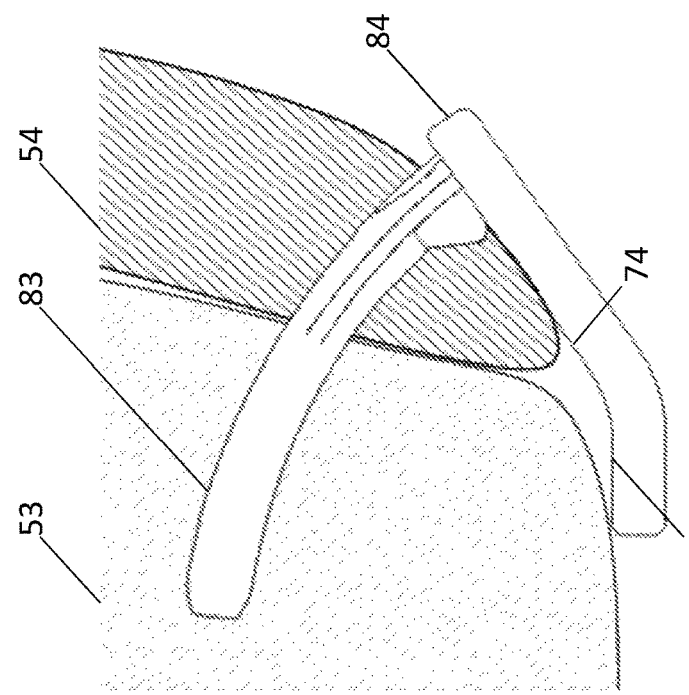
FIG. 23B is a cross-sectional view of the sacrum and ilium to illustrate implantation position of the plate and curved pin shown in FIG. 21.
Figure 23A:
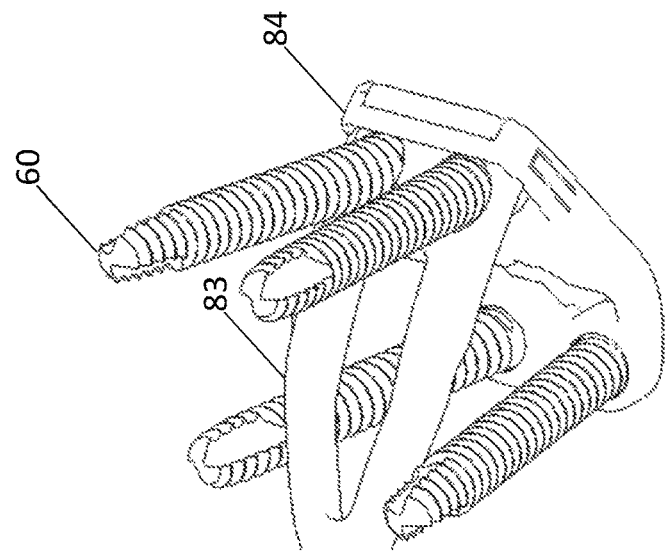
FIG. 23A is a perspective view of an exemplary embodiment of an implant comprising a plate, curved pin, and four bone screws.

FIG. 23A is a perspective view of another exemplary embodiment of an implant comprising a transverse pin, such as transverse pin 83 of FIG. 21; a plate, such as plate 84 of FIG. 22; and four bone screws, such as bone screws 60 of FIG. 17. FIG. 23A illustrates an embodiment with optional features, any of which may be optionally used or substituted with other features in other embodiments discussed herein. As seen in FIG. 23, bone screws 60 include two sacral screws and two iliac screws. FIG. 23B is a cross-sectional view of the sacrum 53 and ilium 54 to illustrate implantation position of plate 84 and curved pin 83 shown in FIG. 21. FIG. 23B illustrates an embodiment with optional features, any of which may be optionally used or substituted with other features in other embodiments discussed herein. As seen in FIG. 23B, plate 84 is placed with sacrum contacting surface 73 adjacent to the sacrum 53 and ilium 54 contacting surface 74 adjacent to ilium 54 and curved pin 83 shown in FIG. 21. Transverse pin 83 is placed through plate 84, extending through ilium 54, and partially extending into the sacrum 53. FIG. 23C is a cross-sectional front view of engagement between the overhang 89 of transverse pin 83 and pocket 93 of plate 84 of FIGS. 21 and 22, respectively. FIG. 23C illustrates an embodiment with optional features, any of which may be optionally used or substituted with other features in other embodiments discussed herein. FIG. 23D is a cross-sectional side view of engagement between rail end 94 of transverse pin 83 and snap 91 of arm 96 of plate 84 of FIGS. 21 and 22, respectively. FIG. 23D illustrates an embodiment with optional features, any of which may be optionally used or substituted with other features in other embodiments discussed herein. As seen in FIG. 23D, snap 91 is a square extension at the lateral end of each arm 96 extending towards the center of plate 84 such that when transverse pin 83 is seated in plate 84, snap 91 blocks rail end 94 to prevent transverse pin 83 from backing out.

Figure 24:
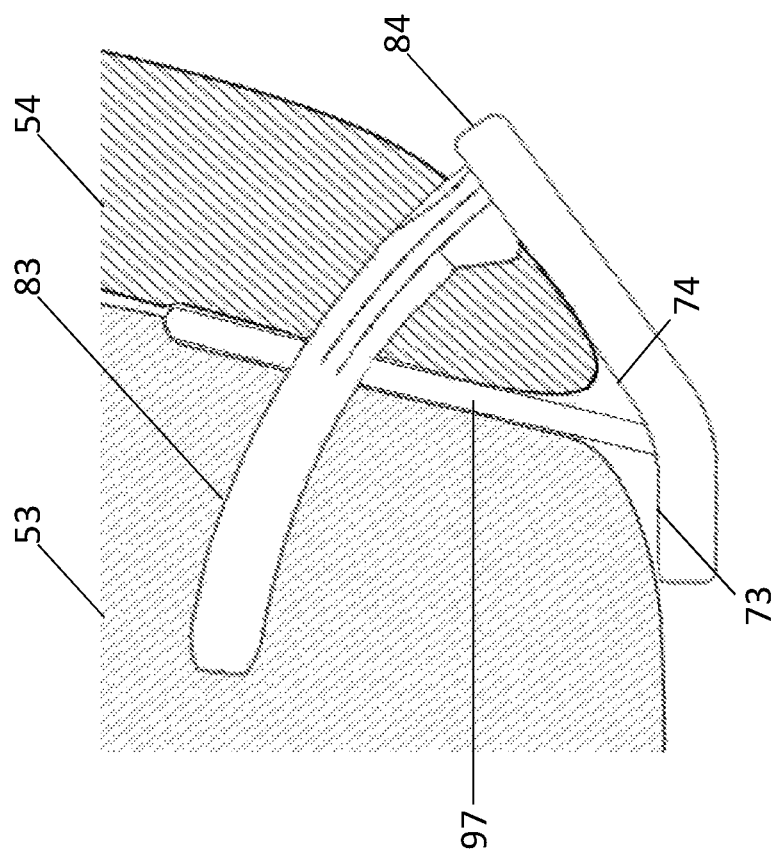
FIG. 24 is a cross-sectional view of the sacrum and ilium to illustrate implantation position of the plate and curved pin shown in FIG. 21 with the addition of bone growth inducing material between the sacrum and the ilium.

FIG. 24 is a cross-sectional view of sacrum 53 and ilium 54. FIG. 24 illustrates an example of an implantation position of plate 84 and curved pin 83 shown in FIG. 21 with the addition of bone growth inducing material 97. FIG. 24 illustrates an embodiment with optional features, any of which may be optionally used or substituted with other features in other embodiments discussed herein. As seen in FIG. 24, bone growth inducing material 97 has been sized to fit through joint visualization window 76 seen in FIG. 22, between sacrum 53 and ilium 54, and through aperture 87 seen in FIG. 21. Optionally, in any embodiments the bone growth inducing material may be integrated within the plate. Optionally, in any embodiments the bone growth inducing material may be integrated within the plate such that the bone growth inducing material may slide into the sacroiliac joint as the plate is being placed. Optionally, in any embodiments the bone growth inducing material may be connected to the plate. Optionally, in any embodiments the bone growth inducing material may be connected to the plate such that the bone growth inducing material may slide into the sacroiliac joint as the plate is being placed. Embodiments having bone growth inducing material that is connected to and/or integrated within the plate may be optionally used or substituted with other features in other embodiments discussed herein.

Figure 25:
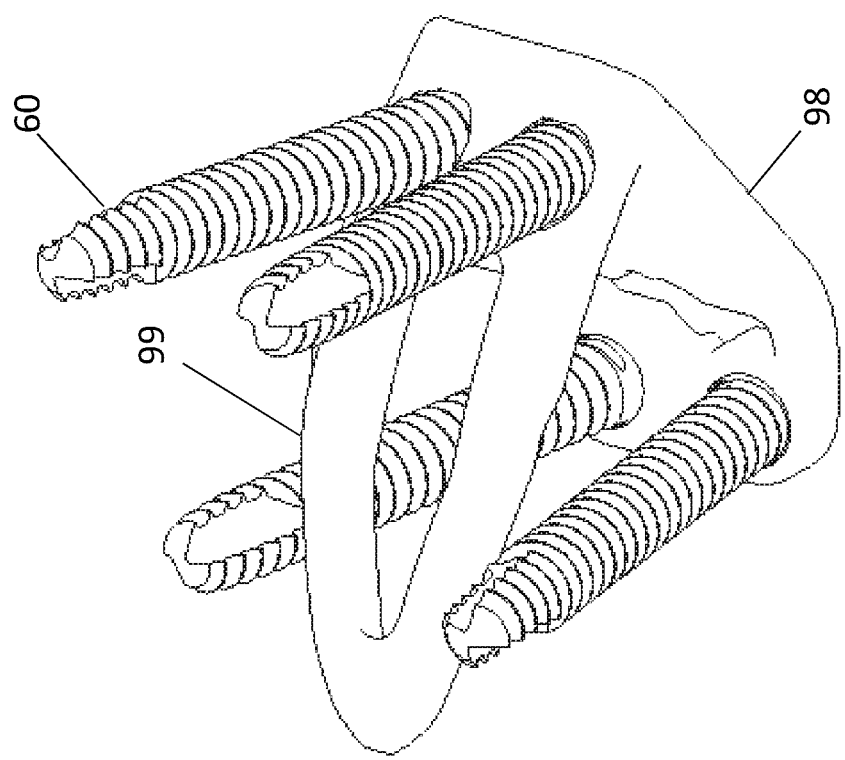
FIG. 25 is a perspective view of an exemplary embodiment of an implant comprising an integrated plate/pin component having a plate component, a curved pin component, and four bone screws.

FIG. 25 is a perspective view of an exemplary embodiment of an implant comprising an integrated plate/pin component having a plate component 98, a curved pin component 99, and four bone screws 60. FIG. 25 illustrates an embodiment with optional features, any of which may be optionally used or substituted with other features in other embodiments discussed herein. In particular, the implant comprises two sacral screws and two iliac screws. As seen in FIG. 25, plate component 98 and pin component 99 of the illustrated integrated pin/plate component are formed of a single body.

Figure 26:
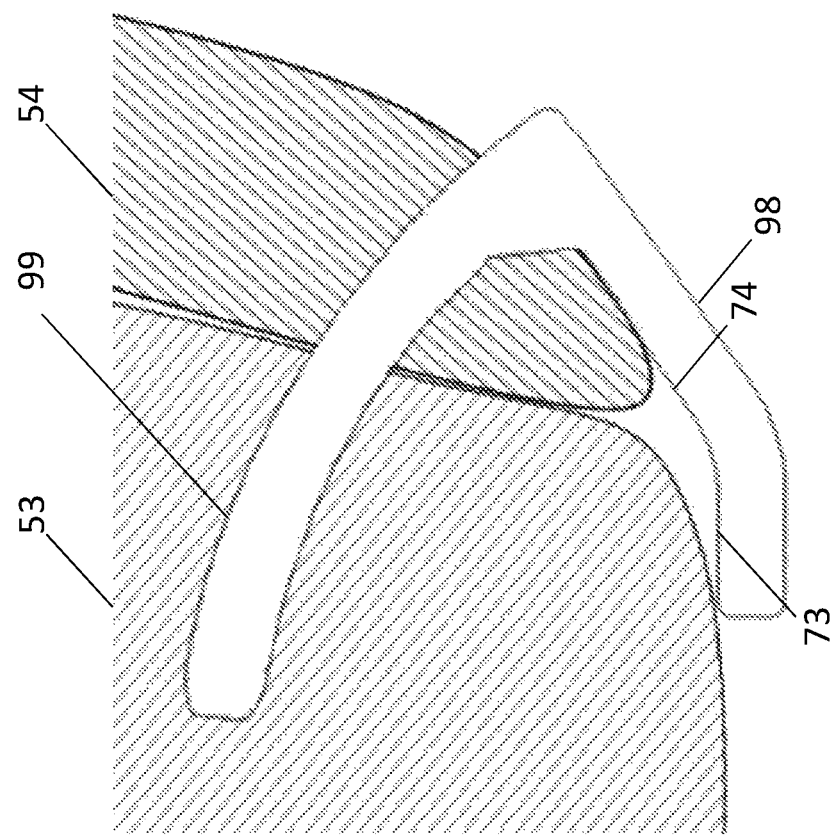
FIG. 26 is a cross-sectional view of the sacrum and ilium to illustrate implantation position of the plate and curved pin shown in FIG. 25.

FIG. 26 is a cross-sectional view of the sacrum 53 and ilium 54 to illustrate implantation position of the plate component 98 and curved pin component 99 shown in FIG. 25. As seen in FIG. 26, plate component 98 is placed with sacrum-contacting surface 73 adjacent to the sacrum 53 and ilium-contacting surface 74 adjacent to ilium 54. Pin component 99 extends through plate component 98, further extending through ilium 54, extending across a sacroiliac joint space between said sacrum 53 and ilium 54, and partially extending into the sacrum 53.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the following claims define the scope of the invention and that methods and structures within the scope of these claims and their equivalents be covered thereby.

What is claimed is:

1. A method of fixation and fusion of a sacroiliac joint comprising an ilium, a sacrum, and a sacroiliac joint space, the method comprising:
   decorticating of said sacroiliac joint;
   broaching a first channel through said ilium, across said sacroiliac joint space, and into said sacrum, wherein said first channel is configured to receive a transverse pin of a sacroiliac joint implant;
   providing bone growth inducing material within said sacroiliac joint space;
   drilling a second channel into said sacrum, wherein said second channel is configured to receive a first sacrum screw of said sacroiliac joint implant, wherein the second channel is adjacent the first channel;

drilling a third channel into said sacrum, wherein said third channel is configured to receive a second sacrum screw of said sacroiliac joint implant, wherein the third channel is adjacent the first channel, and wherein the first channel is between the second channel and the third channel;

placing a plate of said sacroiliac joint implant across said sacroiliac joint space, said plate comprising a sacrum portion and an ilium portion;

inserting said transverse pin through said plate and through said first channel;

inserting said first sacrum screw through said plate and through said second channel; and inserting said second sacrum screw through said plate and through said third channel.

2. The method of claim 1, wherein said providing bone growth inducing material within said sacroiliac joint space is prior to placement of said sacroiliac joint implant.

3. The method of claim 1, wherein said providing bone growth inducing material within said sacroiliac joint space is after placement of said sacroiliac joint implant.

4. The method of claim 1, wherein a portion of said providing bone growth inducing material within said sacroiliac joint space is prior to placement of said sacroiliac joint implant and wherein a portion of providing bone growth inducing material within said sacroiliac joint space is after placement of said bone growth inducing material.

5. The method of claim 1, providing at least a portion of said bone growth inducing material to said sacroiliac joint space through an aperture within said transverse pin.

6. The method of claim 1, wherein placing said plate comprises placing said sacrum portion flush with said posterior surface of a sacrum of a patient.

7. The method of claim 1, wherein placing said plate comprises placing said ilium portion flush with said posterior surface of an ilium of a patient.

8. The method of claim 1, wherein an angle between a bone contacting surface of said sacrum portion and a bone contacting surface of said ilium portion is between 95 degrees and 175 degrees.

9. The method of claim 1, wherein an angle between a bone contacting surface of said sacrum portion and a bone contacting surface of said ilium portion is adjustable.

10. The method of claim 1, wherein an angle between said sacrum portion and said ilium portion is configured to match anatomy of a particular patient.

11. The method of claim 1, further comprising:

drilling a third channel into said ilium, wherein said third channel is configured to receive an ilium screw of said sacroiliac joint implant; and inserting said ilium screw through said plate and through said third channel.

12. A method of fixation and fusion of a sacroiliac joint comprising an ilium, a sacrum, and a sacroiliac joint space, the method comprising:

decorticating of said sacroiliac joint;

broaching a first channel through said ilium, across said sacroiliac joint space, and into said sacrum, wherein said first channel is configured to receive a transverse pin of a sacroiliac joint implant;

providing bone growth inducing material within said sacroiliac joint space;

drilling a second channel into said sacrum, wherein said second channel is configured to receive a sacrum screw of said sacroiliac joint implant;

placing a plate of said sacroiliac joint implant across said sacroiliac joint space, said plate comprising a sacrum portion and an ilium portion;

inserting said transverse pin through said plate and through said first channel;

inserting said sacrum screw through said plate and through said second channel; and inserting said sacrum screw within a receiving component of said transverse pin.

\* \* \* \* \*